(12) United States Patent
Ohashi

(10) Patent No.: US 9,623,410 B2
(45) Date of Patent: Apr. 18, 2017

(54) SEGMENTABLE CONTAINER AND METHOD OF SEGMENTING SUBSTANCE CONTAINED IN CONTAINER

(71) Applicant: SHIMADZU CORPORATION, Kyoto-shi, Kyoto (JP)

(72) Inventor: Tetsuo Ohashi, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 14/387,116

(22) PCT Filed: Feb. 12, 2013

(86) PCT No.: PCT/JP2013/053241
§ 371 (c)(1),
(2) Date: Sep. 22, 2014

(87) PCT Pub. No.: WO2013/145901
PCT Pub. Date: Oct. 3, 2013

(65) Prior Publication Data
US 2015/0098874 A1   Apr. 9, 2015

(30) Foreign Application Priority Data

Mar. 30, 2012 (JP) .................................. 2012-081233

(51) Int. Cl.
*B01L 3/00* (2006.01)
*B65D 17/00* (2006.01)
*G01N 30/60* (2006.01)

(52) U.S. Cl.
CPC ............... *B01L 3/52* (2013.01); *B01L 3/5021* (2013.01); *B01L 3/502784* (2013.01);
(Continued)

(58) Field of Classification Search
CPC ............. G01N 30/02; G01N 2030/022; G01N 2030/025; G01N 2030/027
See application file for complete search history.

(56) References Cited

U.S. PATENT DOCUMENTS 5,294,336 A * 3/1994 Mizuno ................. B01D 15/08
210/143
6,121,055 A * 9/2000 Hargreaves ............. B01L 3/502
435/2
(Continued)

FOREIGN PATENT DOCUMENTS

CN       103619727 A       3/2014
JP       8-206177 A        8/1996
(Continued)

OTHER PUBLICATIONS http://www.rhinometro.com/RM-v09/Pages/trucks_faqs.html, Obtained using Wayback Machine from Jan. 26, 2012.*
(Continued)

*Primary Examiner* — Sean E Conley
*Assistant Examiner* — Matthew Krcha
(74) *Attorney, Agent, or Firm* — Cheng Law Group, PLLC

(57) ABSTRACT

Provided are a simple, quick, and low-processing cost method capable of reliably separating part of an accommodated substance accommodated in a vessel only by simple mechanical operation while maintaining a hermetically-sealed state without any contact with an outside atmosphere, as well as a vessel with which the method may be used. A separable vessel comprises a first vessel portion, a second vessel portion which is contiguous with the first vessel portion, a fracture-inducing portion formed between the first vessel portion and the second vessel portion, and a self-fusing material provided on an outer surface so as to cover
(Continued)

the fracture-inducing portion; and may contain an accommodated substance therein.

29 Claims, 10 Drawing Sheets

(52) U.S. Cl.
CPC ...... *B65D 17/00* (2013.01); *B01L 2200/0668* (2013.01); *B01L 2200/0689* (2013.01); *B01L 2300/087* (2013.01); *B01L 2300/0838* (2013.01); *B01L 2300/0858* (2013.01); *B01L 2400/043* (2013.01); *B01L 2400/0409* (2013.01); *G01N 30/60* (2013.01); *Y10T 156/1005* (2015.01)

(56) References Cited

U.S. PATENT DOCUMENTS

| | | |
|---|---|---|
| 8,641,990 B2 | 2/2014 | Andersen et al. |
| 2006/0257665 A1* | 11/2006 | Bennett .............. B32B 33/00 428/411.1 |
| 2009/0269246 A1 | 10/2009 | Hasegawa |
| 2010/0303688 A1* | 12/2010 | Andersen .............. A01N 1/02 422/549 |
| 2013/0043150 A1 | 2/2013 | Ohashi |
| 2013/0065236 A1 | 3/2013 | Ohashi et al. |
| 2014/0124446 A1 | 5/2014 | Ohashi et al. |

FOREIGN PATENT DOCUMENTS

| | | | |
|---|---|---|---|
| JP | 8-324601 A | 12/1996 | |
| JP | 10-248905 A | 9/1998 | |
| JP | 2000-70763 A | 3/2000 | |
| JP | 2004-26261 A | 1/2004 | |
| JP | 2011-510266 A | 3/2011 | |
| JP | 2011-229488 A | 11/2011 | |
| JP | 2011-232260 A | 11/2011 | |
| WO | WO 2006127651 A2 * | 11/2006 | ....... B60K 15/03177 |
| WO | WO-2006/132041 A1 | 12/2006 | |
| WO | WO-2012/176598 A1 | 12/2012 | |

OTHER PUBLICATIONS

Written Opinion of the International Searching Authority (PCT/ISA/237 for Application No. PCT/JP2013/053241 mailed May 21, 2013 (English Translation mailed Oct. 9, 2014).

International Search Report for the Application No. PCT/JP2013/053241 mailed May 21, 2013.

* cited by examiner

SEGMENTABLE CONTAINER AND METHOD OF SEGMENTING SUBSTANCE CONTAINED IN CONTAINER

TECHNICAL FIELD

The present invention relates to a method for separating and collecting an accommodated substance or part thereof from a vessel-shaped structure accommodating one or more of a liquid, a solid, a gas, and a dispersion system without contact with outside air or without leakage to the outside, and a vessel and device suitable for the method.

Particularly, the present invention relates to a method for easily separating and collecting an accommodated substance or part thereof from a vessel-shaped structure accommodating one or more of a liquid, a solid, a gas, and a dispersion system in a hermetically-sealed state while maintaining the hermetically-sealed state, and a vessel and device suitable for the method.

The present invention can be used to separate and collect part or all of a liquid, a solid, a gas, or the like accommodated in one or more spaces in a vessel while maintaining a hermetically-sealed state. The present invention is useful in food and medical fields requiring aseptic manipulation, manufacturing and processing fields handling hazardous substances or radioactive substances, and semiconductor and microdevice manufacturing fields requiring a dust-free environment.

BACKGROUND ART

As structures (specifically, hermetically-sealed vessels) for storing an accommodated substance in a hermetically-sealed state in order to avoid chemical actions such as oxidation by an outside atmosphere, diffusion of hazardous substances, contaminants, or microorganisms contained in vessels to the outside, or entry of hazardous substances, contaminants, or microorganisms into vessels from the outside, cans, bottles, ampules, vials, and hermetically-sealed packages using resin films or sheets are conventionally used.

A typical example of a structure, from which part of an object substance accommodated therein in a hermetically-sealed state can be separated while being the hermetically sealed state, includes a sheet of pharmaceutical tablets disclosed in JP-A-8-206177 (Patent Document 1) and JP-A-10-248905 (Patent Document 2). In the case of a structure such as a sheet of tablets, accommodated substances (tablets) are previously hermetically sealed in their respective independent spaces, and therefore do not come into contact with each other in the structure.

JP-A-2011-229488 (Patent Document 3) discloses a hermetically-sealed nucleic acid amplification reaction system in which a nucleic acid amplification reaction is performed in a droplet of a nucleic acid amplification reaction liquid encapsulated by a droplet encapsulating medium while the droplet is moved in a vessel filled with the droplet encapsulating medium insoluble or poorly soluble in the nucleic acid amplification reaction liquid.

JP-A-2011-232260 (Patent Document 4) discloses a hermetically-sealed manipulation system in which a substance in a droplet of an aqueous liquid encapsulated by a gel-state droplet encapsulating medium is manipulated while the droplet is moved in a vessel filled with the gel-state droplet encapsulating medium insoluble or poorly soluble in the aqueous liquid.

PRIOR ART DOCUMENTS

Patent Documents

Patent Document 1: JP-A-8-206177
Patent Document 2: JP-A-10-248905
Patent Document 3: JP-A-2011-229488
Patent Document 4: JP-A-2011-232260

SUMMARY OF THE INVENTION

Problems to be Solved by the Invention

When used only for storage of an object substance to be separated, a structure may be configured like the sheet of tablets disclosed in the Patent Document 1 and the Patent Document 2 so that object substances (tablets) are accommodated in their respective independent spaces.

However, when being not just a storage vessel but a vessel used to previously subject an object substance to be separated to the process of physical, chemical, and/or biological manipulation, a structure is required to allow both an object substance and a manipulation medium to be present in the same vessel so that the object substance can come into contact with the manipulation medium that provides a field for performing the above-described manipulation.

For example, in a structure for performing both physical, chemical, or biochemical manipulation and collection of an object substance subjected to the manipulation, both a manipulation medium for performing physical, chemical, or biochemical manipulation and a collection medium for collecting a final product may be present in the same vessel. In the case of such a structure, even after the completion of various manipulations and collection, an object substance after the manipulations and a medium used for the manipulations are present in the same interior space. Therefore, in order to prevent unnecessary mixing of both present in the interior space, there is a case where only a collection medium, in which the object substance after the manipulations is present, is required to be separated.

When such separation is performed by, for example, simply cutting the structure between a part accommodating a manipulation medium (manipulation portion) and a part accommodating a collection medium (collection portion), both the manipulation portion and the collection portion separated from each other have an open end so that the accommodated substance is exposed to an outside atmosphere. Even when each open end is covered with airtight stoppers immediately after the separation, it is impossible to avoid contact between the accommodated substance and an outside atmosphere or diffusion of the accommodated substance to an outside atmosphere.

Therefore, in the above case, there is a case where part of the accommodated substance is further required to be separated without any contact with an outside atmosphere. This applies to, for example, a case where a reaction product obtained by a biochemical reaction performed in the structure is one that is easily oxidized by oxygen contained in an outside atmosphere, a case where the reaction product is one that is easily contaminated by exposure to an outside atmosphere, or a case where the reaction product is one that contaminates an outside atmosphere.

It is considered that, as an example of satisfying the above requirement, provided is a structure including a manipulation portion accommodating a manipulation medium and a collection portion accommodating a collection medium for an object substance after manipulation, wherein a physical separation system with an opening and closing system, such as a shutter, is formed between the manipulation portion and the collection portion. However, when the structure satisfying the above requirement is required to be a small vessel such as a microdevice, it is not easy for the vessel to have such a complicated system.

Also in the case of each of the vessels disclosed in Patent Document 3 and Patent Document 4, a nucleic acid amplification reaction product produced in the vessel or a substance after the completion of manipulation in the vessel cannot be taken out from the vessel while being maintained in a hermetically-sealed state.

Therefore, an object of the present invention is to provide simple, quick, and low-processing cost means capable of reliably separating part (for example, a collection liquid) of an accommodated substance (for example, a manipulation medium for performing physical, chemical, and/or biochemical treatment and a collection liquid containing a target substance) accommodated in a vessel only by simple mechanical operation while maintaining a hermetically-sealed state without any contact with an outside atmosphere.

Means for Solving to the Problems

The present inventors have intensively studied, and as a result, found that the above object of the present invention can be achieved by accommodating a substance to be accommodated in a vessel having a fracture-inducing portion formed in a position where the vessel should be separated and a self-fusing material provided so as to cover the fracture-inducing portion. This finding has led to the completion of the present invention.

The present invention includes the following.
(1) a Separable Vessel Comprising:
   a fracture-inducing portion formed in a position where fracture should be caused to separate the vessel into a first vessel portion and a second vessel portion; and
   a self-fusing material provided on an outer surface so as to cover the fracture-inducing portion.
(2) The vessel according to the above (1), containing an accommodated substance therein.
(3) The vessel according to the above (2), being a manipulation vessel for subjecting a sample containing an object component to a predetermined manipulation therein, wherein
   the first vessel portion is a manipulation portion for subjecting a sample containing an object component to a predetermined manipulation,
   the second vessel portion is a collection portion for collecting a target substance from the manipulation portion, and
   the accommodated substance is a manipulation medium selected from the group consisting of a liquid, a solid, a gas, and a dispersion system, as a field for performing manipulation to which the object component is to be subjected.
(4) The vessel according to the above (3), wherein the manipulation portion comprises a column for chromatography, and the manipulation medium comprises a filling material for chromatography and a developing solvent.
   A specific example of an embodiment of the above (4) is shown in FIG. 1(1).
(5) The vessel according to the above (3), having a tubular shape, wherein the manipulation medium is a multi-layered object in which layers of an aqueous liquid and a gel are alternately stacked in a longitudinal direction.
   A specific example of an embodiment of the above (5) is shown in FIG. 1(2).
(6) The vessel according to the above (3), wherein the manipulation medium comprises a droplet encapsulating medium and an encapsulated aqueous droplet.
   A specific example of an embodiment of the above (6) is shown in FIG. 2.
(7) The vessel according to any one of the above (1) to (6), further comprising a protective member on an outer surface of the self-fusing material.
(8) The vessel according to any one of the above (1) to (7), wherein the self-fusing material has a thickness of 0.01 to 5 mm per 1 $cm^2$ of area of a plane within an outer periphery of the vessel.
(9) The vessel according to any one of the above (1) to (8), wherein the fracture-inducing portion is a portion having been subjected to treatment to reduce a wall thickness of the vessel and/or treatment to reduce the material strength of the vessel.
   A preferred example of the portion having been subjected to treatment to reduce a wall thickness of the vessel is a groove (fracture-inducing groove) formed in the surface of the vessel. The treatment to reduce the material strength of the vessel does not include the treatment to reduce a wall thickness of the vessel.
   The fracture-inducing groove may have a depth 0.3 to 0.6 times the thickness of the vessel.
(10) The vessel according to any one of the above (1) to (9), wherein the self-fusing material is selected from the group consisting of isobutylene-isoprene copolymers, ethylene-propylene-diene copolymers, polyisobutylene, paraffin, polyvinyl acetate, polyurethane, polydimethyl siloxane, ethylene propylene copolymers, hydrogel polymers, (meth)acrylic acid ester copolymers, silicone rubber, and natural rubber.
(11) The vessel according to any one of the above (1) to (10), wherein the self-fusing material is a thermoplastic resin having a glass transition temperature of 50° C. to 180° C.
(12) The vessel according to the above (11), wherein the thermoplastic resin is selected from the group consisting of polyethylene, polypropylene, polystyrene, ethylene-vinyl acetate copolymers, polyacetal, polymethyl methacrylate, polyvinyl alcohol, polyvinyl chloride, vinyl chloride-vinyl acetate copolymers, vinyl chloride-acrylic acid ester copolymers, polyvinylidene chloride, and vinylidene chloride-acrylic acid ester copolymers.
(13) A manipulation device for manipulating an object component in a vessel, comprising:
   the vessel according to any one of the above (2) to (12);
   magnetic particles that should capture and transport an object component; and
   magnetic field application means for applying a magnetic field to the vessel so that the magnetic particles can be moved from an inside of the first vessel portion to an inside of the second vessel portion.
(14) A method for separating a substance accommodated in a vessel, the vessel being a separable vessel comprising: a fracture-inducing portion formed in a position where fracture should be caused to separate the vessel into a first vessel portion and a second vessel portion; and a self-fusing material provided on an outer surface so as to cover the fracture-inducing portion, and the vessel containing an accommodated substance therein,
   the method comprising subjecting the vessel to the following steps:
   (i) applying an external force to the vessel to cause fracture in a position of the fracture-inducing portion so that the first vessel portion and the second vessel portion are separated from each other to form fracture openings of the respective vessel portions but are connected to each other through the self-fusing material;

(ii) pulling the first vessel portion and the second vessel portion away from each other to extend the self-fusing material;

(iii) fusing the extended self-fusing material together so that a space between the first vessel portion and the second vessel portion is blocked to separate the accommodated substance; and (iv) cutting a fused part of the self-fusing material to separate the vessel into a first separated structure that includes the first vessel portion whose fracture opening is closed by the self-fusing material and that contains one of the separated parts of the accommodated substance, and a second separated structure that includes the second vessel portion whose fracture opening is closed by the self-fusing material and that contains the other separated part of the accommodated substance.

(15) The method according to the above (14), wherein the external force in the step (i) is a twisting force around an axis in a direction in which the first vessel portion and the second vessel portion are to be pulled away from each other in the step (ii).

(16) The method according to the above (15), wherein the twisting force is 8 to 11 cN·m.

(17) The method according to any one of the above (14) to (16), wherein in the steps (iii) and (iv), the fusion of the extended self-fusing material together and the cutting of the fused part are performed by twisting the first vessel portion and the second vessel portion around an axis in a direction in which the first vessel portion and the second vessel portion have been pulled away from each other.

A specific example of an embodiment of the above (17) is shown in FIG. 3.

(18) The method according to any one of the above (14) to (16), wherein the extended self-fusing material is fused together by externally pinching with pressure-bonding means in the step (iii), and the fused part is cut with cutting means in the step (iv).

(19) The method according to the above (18), wherein the pressure-bonding means and the cutting means are separately prepared.

A specific example of an embodiment of the above (19) is shown in FIG. 4.

(20) The method according to the above (18), wherein the pressure-bonding means comprises a pair of pressure-bonding members; and the cutting means is prepared in such a manner that a flat plate-shaped cutting blade is provided so as to be able to penetrate into one member of the pair of pressure-bonding members, and the cutting of the fused part in the step (iv) is performed by allowing the flat plate-shaped cutting blade to penetrate the one of the pair of pressure-bonding members.

A specific example of an embodiment of the above (20) is shown in FIG. 5.

(21) The method according to any one of the above (14) to (20), wherein the vessel to be subjected to the steps (i) to (iv) further comprises a protective member on an outer surface of the self-fusing material.

(22) The method according to any one of the above (14) to (21), wherein the self-fusing material has a thickness of 0.01 to 5 mm per 1 cm$^2$ of area of a plane within an outer periphery of the vessel.

(23) The container according to any one of the above (14) to (22), wherein the fracture-inducing portion is a portion having been subjected to treatment to reduce a wall thickness of the vessel and/or treatment to reduce the material strength of the vessel.

(24) The method according to any one of the above (14) to (23), wherein the self-fusing material is selected from the group consisting of isobutylene-isoprene copolymers, ethylene-propylene-diene copolymers, polyisobutylene, paraffin, polyvinyl acetate, polyurethane, polydimethyl siloxane, ethylene propylene copolymers, hydrogel polymers, (meth)acrylic acid ester copolymers, silicone rubber, and natural rubber.

(25) The method according to any one of the above (14) to (24), wherein the self-fusing material is a thermoplastic resin having a glass transition temperature of 50° C. to 180° C.

(26) The method according to the above (25), wherein the thermoplastic resin is selected from the group consisting of polyethylene, polypropylene, polystyrene, ethylene vinyl acetate copolymers, polyacetal, polymethyl methacrylate, polyvinyl alcohol, polyvinyl chloride, vinyl chloride-vinyl acetate copolymers, vinyl chloride-acrylic acid ester copolymers, polyvinylidene chloride, and vinylidene chloride-acrylic acid ester copolymers.

(27) The method according to any one of the above (14) to (26), wherein the vessel is a manipulation vessel for subjecting a sample containing an object component to a predetermined manipulation therein, the first vessel portion is a manipulation portion for subjecting a sample containing an object component to a predetermined manipulation, the second vessel portion is a collection portion for collecting a target substance from the manipulation portion, and the accommodated substance is a manipulation medium selected from the group consisting of a liquid, a solid, a gas, and a dispersion system, as a field for performing manipulation to which the object component is to be subjected, the method further comprising, prior to the step (i), subjecting the manipulation vessel to the step of subjecting the sample to a predetermined manipulation and collecting the target substance.

(28) The method according to the above (27), wherein the manipulation portion comprises a column for chromatography, and the manipulation medium comprises a filling material for chromatography and a developing solvent.

A specific example of an embodiment of the above (28) is shown in FIG. 4.

(29) The method according to the above (27), wherein the manipulation vessel has a tubular shape, and the manipulation medium is a multi-layered object in which layers of an aqueous liquid and a gel are alternately stacked in a longitudinal direction.

A specific example of an embodiment of the above (29) is shown in FIG. 7.

(30) The method according to the above (27), wherein the manipulation medium comprises a droplet encapsulating medium and an encapsulated aqueous droplet.

A specific example of an embodiment of the above (30) is shown in FIG. 8.

(31) The method according to the above (29) or (30), wherein the manipulation portion has an openably-closed sample supply portion for supplying a sample into the manipulation vessel, and after a step of supplying the sample, the accommodated substance is maintained in a completely hermetically-sealed state until the step (iv) is finished.

Effects of the Invention

According to the present invention, a simple, quick, and low-processing cost method can be provided which is capable of reliably separating part (for example, a collection liquid) of an accommodated substance (for example, a manipulation medium for performing physical, chemical, and/or biochemical treatment and a collection liquid containing a target substance) accommodated in a vessel only by simple mechanical operation while maintaining a hermetically-sealed state without any contact with an outside atmosphere, and a vessel that can implement such a method can be provided.

According to the present invention, the production cost of the vessel is low because the vessel does not need to have a complicated opening and closing system. Further, part of the vessel can be separated and collected by a simple system, and therefore the vessel can be applied to a miniaturized device.

DESCRIPTION OF REFERENCE SIGNS

Figure 1:
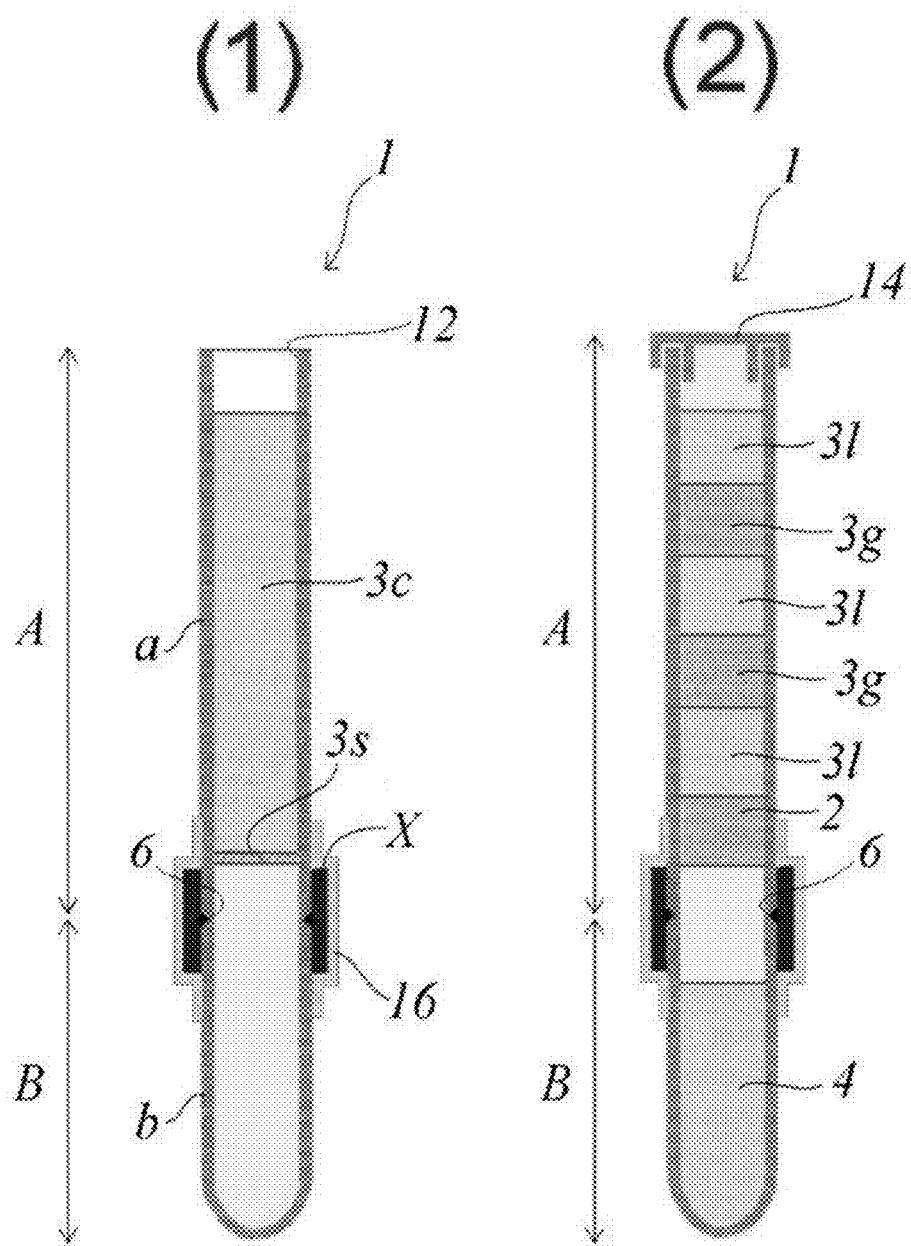
FIGS. 1(1) and 1(2) are vertical sectional views of examples of a vessel according to the present invention.

1: vessel (manipulation vessel)
a: first vessel portion
b: second vessel portion
X: self-fusing material
A: manipulation portion
B: collection portion
31: aqueous liquid layer
3g, 2g: gel layer
3d: aqueous droplet
5: droplet encapsulating medium
6: fracture-inducing groove
11a, 11b: fracture opening
12: open end (sample supply portion)
16: protective member
31: pressure-bonding member
32: cutting means
41, 42: flat plate-shaped cutting blade (41: cutter main body, 42: cutting edge)
61: magnetic particles
63: magnetic field applying means (magnet)

MODE FOR CARRYING OUT THE INVENTION

[1. Basic Structure of Vessel]

Figure 2:
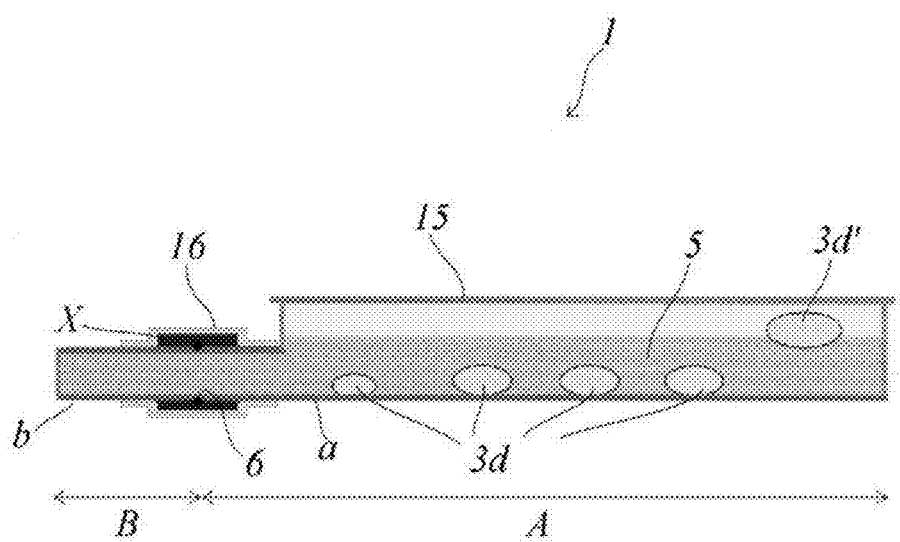
FIG. 2 is a vertical sectional view of another example of the vessel according to the present invention.

Examples of a vessel according to the present invention are shown in FIGS. 1 and 2. FIGS. 1 and 2 are sectional views of the vessel. A vessel 1 according to the present invention includes a first vessel portion a and a second vessel portion b. The first vessel portion a and the second vessel portion b are continuous and integral with each other, and a single interior space is created within the vessel. A fracture-inducing portion 6 (fracture-inducing groove) is formed in the outer surface of the vessel. The fracture-inducing groove 6 is located at the boundary between the first vessel portion a and the second vessel portion b. Further, a self-fusing material X is provided on the outer surface of the vessel so as to cover the fracture-inducing groove 6.

The shape of the vessel is not particularly limited. For example, the sectional shape of the vessel may be an almost circle, a segment of a circle, a polygon, or the like. More specifically, the vessel may have, for example, a blind tube shape as shown in FIG. 1(1) and FIG. 1(2), or a deformed rectangular shape as shown in FIG. 2, or another shape.

The vessel 1 may have an open end 12 on the first vessel portion a-side. Part or whole of the open end 12 may be openably closed. FIG. 1(2) shows an example in which part of the open end is openably closed. In the case of this embodiment, the use of a septum 14 having the function of a check valve makes it possible to supply a sample by puncture with an injection needle in a state close to a hermetically-sealed state. Further, FIG. 2 shows an example in which whole of the open end is openably closed. In the case of this embodiment, a lid 15 that covers the open end 12 can be used.

Closing the open end 12 is preferred in that a complete closed system can be constructed in the vessel 1.

The fracture-inducing portion (fracture-inducing groove 6 in the examples shown in the drawings) is located at the boundary between the first vessel portion a and the second vessel portion b. The fracture-inducing portion is a portion subjected to stress concentration due to an appropriate external force applied from the outside of the vessel. The stress concentration effectively induces fracture. The fracture-inducing portion is preferably formed over the entire outer periphery of the vessel. Preferably, the fracture-inducing portion may be formed to have such a strength that, when a twisting force is applied as an external force from the outside of the vessel to cause fracture, fracture occurs at about 8 to 11 cN·m.

The fracture-inducing portion may be embodied as a portion having been subjected to treatment to reduce the wall thickness of the vessel as in the case of the fracture-inducing groove 6 illustrated in the drawing, or may be embodied as a portion having been subjected to treatment to locally reduce the material strength of the vessel.

The cross-section of the fracture-inducing groove may have either a U or V shape. The size of the groove can be appropriately determined by those skilled in the art depending on the shape of the vessel, the thickness of the vessel, the type of external force-applying means, etc. so that fracture can be effectively induced. For example, the depth of the fracture-inducing groove may be 0.3 to 0.6 times the thickness of the vessel (for example, 0.1 to 10 mm, preferably 0.5 to 3.0 mm). If the depth exceeds the above range, an external force required for separation can be made small, but because of that, durability tends to be a problem. If the depth is less than the above range, a great external force is required at the time of separating the vessel. In addition, it is difficult to effectively concentrate stress on the fracture-inducing groove, which tends to cause deformation of the whole vessel. When the vessel is made of a soft material, the fracture-inducing groove may be formed to be relatively shallow. In the present invention, the fracture-inducing groove is preferably formed to have a V-shaped cross-section. In this case, the fracture-inducing groove having a V-shaped cross-section is formed so that the angle of the V shape is preferably 15° to 90°, for example, 60°.

An example of the treatment to locally reduce the material strength of the vessel includes treatment in which the mechanical strength of the material of the vessel is reduced (the material of the vessel is fatigued) by applying physical stress, electricity, or radiation to the material of part of the vessel where the fraction-inducing portion should be formed. Such treatment makes it possible to embody the fracture-inducing portion as, for example, a portion having a plurality of fine cracks. An example of the treatment also includes treatment in which the material of part of the vessel where the fracture-inducing portion should be formed is brought into contact with an organic solvent to be swelled. Such treatment makes it possible to embody the fracture-inducing portion as a portion having a large number of micropores or a softened portion.

Another example of the treatment to locally reduce the material strength of the vessel includes treatment to chemically change the material of the vessel to produce a low-strength product. An example includes treatment in which the material of part of the vessel where the fracture-inducing portion should be formed is brought into contact and is allowed to react with a corrosive chemical agent. Such treatment makes it possible to embody the fracture-inducing portion as a portion made of a corrosion product.

The depth of the portion having reduced material strength from the surface of the vessel may be 0.3 to 0.6 times the thickness of the vessel as in the case of the above-described fracture-inducing groove.

A material of the vessel is not particularly limited. Examples of the material include resin materials such as polypropylene, polyethylene, fluorine resins (e.g., Teflon (registered trademark)), polyvinyl chloride, polystyrene, polycarbonate, acrylonitrile butadiene copolymers (ABS resins), acrylonitrile styrene copolymers (AS resins), acrylic resins, polyvinyl acetate, polyethylene terephthalate, and cyclic polyolefins. Alternatively, the material may be ceramic, glass, silicone, or metal.

An accommodated substance may be contained in the interior space created in the vessel. The form of the accommodated substance is not particularly limited, and can be appropriately determined by those skilled in the art depending on the intended use of the structure. That is, as the accommodated substance, one or more are arbitrarily selected from the group consisting of a liquid, a solid, a gas, and a dispersion system.

The vessel 1 according to the present invention may be used for the purpose of manipulating an object substance therein. When used as a vessel for manipulating an object substance, the vessel 1 according to the present invention may be particularly sometimes referred to as a manipulation vessel. In the manipulation vessel 1, a portion corresponding to the first vessel portion a may be sometimes referred to as a manipulation portion A, and a portion corresponding to the second vessel portion b may be sometimes referred to as a collection portion B. The manipulation vessel 1 may have a sample supply portion for externally supplying a sample containing an object component to be manipulated. The sample supply portion may be the open end 12 provided on the manipulation portion A side. As has already been described, the open end 12 may be open or may be openably closed from the viewpoint of hermeticity.

The accommodated substance in the manipulation vessel 1 includes a manipulation medium as a field for performing manipulation to which an object component is to be subjected. For example, when the manipulation portion A is a column for chromatography as illustrated in FIG. 1(1), the manipulation medium may comprise a filling material for chromatography and a developing solvent 3c. Further, for example, when the manipulation vessel 1 has a tubular shape as illustrated in FIG. 1(2), the manipulation medium may be a multi-layered object in which aqueous liquid layers 31 and gel layers 3g and 2g are alternately stacked in a longitudinal direction. Further, for example, when the manipulation vessel 1 has such a shape as illustrated in FIG. 2, the manipulation medium may comprise a droplet encapsulating medium 5 and an aqueous droplet 3d encapsulated thereby and/or an aqueous droplet 3d' held thereby. The accommodated substance in the manipulation vessel 1 will be described later in detail in Section 4.

[2. Self-Fusing Material]

In the present invention, the self-fusing material refers to a substance that easily deforms by being present in a semi-solid state and that has the property of mixing and fusing together by pressure contact of the self-fusing material (self-fusibility). Due to such a property, the self-fusing material can fill a narrow gap and can come into close contact with an object without any gap even when an adhesive or a pressure-sensitive adhesive is not used. Therefore, the self-fusing material can come into close contact with the open end, thereby hermetically sealing the open end.

The self-fusibility may be, for example, one developed at ordinary temperature (e.g., 20° C.±15° C.) or one developed by heating (e.g., at 50 to 180° C. or 50 to 150° C.).

The self-fusing material is widely known to those skilled in the art, and is not particularly limited. For example, the self-fusing material may be selected from the group consisting of isobutylene-isoprene copolymers (butyl rubber), ethylene-propylene-diene copolymers, polyisobutylene, paraffin, polyvinyl acetate, polyurethane, polydimethylsiloxane, ethylene propylene copolymers, hydrogel polymers, (meth)acrylic acid ester copolymers (which may be in the form of (meth)acrylic pressure-sensitive adhesive or acrylic foam), silicone rubber, and natural rubber. These self-fusing materials may be used singly or in combination of two or more thereof. The above-mentioned self-fusing materials are preferred in point of being capable of having self-fusibility at ordinary temperature. Among the above-mentioned self-fusing materials, for example, an isobutylene-isoprene copolymer is preferably used in the present invention.

On the other hand, an example of the self-fusing material in which self-fusibility is developed by heating includes a thermoplastic resin having a glass transition temperature of 50° C. to 180° C. or 50 to 150° C. Such a thermoplastic resin may be selected from the group consisting of polyethylene, polypropylene, polystyrene, ethylene vinyl acetate copolymers, polyacetal, polymethyl methacrylate, polyvinyl alcohol, polyvinyl chloride, vinyl chloride-vinyl acetate copolymers, vinyl chloride-acrylic acid ester copolymers, polyvinylidene chloride, and vinylidene chloride-acrylic acid ester copolymers. These self-fusing materials may be used singly or in combination of two or more thereof.

Further, the self-fusing material in which self-fusibility is developed by heating may be used in combination with the above-described substance having self-fusibility at ordinary temperature.

As shown in FIG. 1, the self-fusing material X forms a layer on the outer surface of the vessel-shaped structure 1 so as to cover the fracture-inducing groove 6 formed between the first vessel portion a and the second vessel portion b and its surroundings. For example, the layer can be formed by preparing a tape-shaped self-fusing material and wrapping the tape-shaped self-fusing material around the outer peripheral surface of the vessel so that the self-fusing material is integrated with the vessel by self-fusion. The layer of the self-fusing material shall have such a thickness that a separation method according to the present invention can be achieved, and the thickness of the layer is not particularly limited because the required thickness of the layer varies depending on the area of a plane within the outer periphery of part of the vessel that should be covered with the layer. However, the thickness of the layer may be, for example, 0.01 to 5 mm or 0.1 to 5 mm per 1 square centimeter of area of a plane within the outer periphery of the vessel. Here, the area of a plane within the outer periphery of the vessel refers to the area of a plane enclosed by the outer periphery of the cross-section of the vessel not including the fracture-inducing groove. More specifically, the layer of the self-fusing material may have a thickness of 0.001 to 3 mm or 0.1 to 0.5 mm. If the thickness exceeds the above range, there is a tendency that an excessive force is required for separating the vessel-shaped structure or the need for excessively strongly providing a protective member, which will be described later, arises. If the thickness is less than the above range, there is a tendency that a membrane of the self-fusing material is easily broken when the vessel-shaped structure is separated or a membrane of the self-fusing material closing the separated vessel-shaped structure is too thin.

Means for forming a layer of the self-fusing material on the vessel is not limited to taping with a tape-shaped self-fusing material. For example, a layer of the self-fusing material can be formed by dissolving the self-fusing material in a volatile organic solvent and applying the solution onto a target part of the vessel. For example, butyl rubber is dissolved in various volatile organic solvents such as toluene, xylene, and tetrahydrofuran, and has high viscosity in a high concentration, and therefore a layer of the self-fusing material can be formed by application with high reproducibility. After being dried, the layer of the self-fusing material exhibits the same self-fusibility as that formed by the taping method.

In the vessel 1 of the present invention, a protective member 16 for protecting the self-fusing material X may be further provided on the outer surface of the self-fusing material X. The protective member may be provided for the purpose of preventing the contamination of the surface of the self-fusing material and preventing cold flow that is a phenomenon unique to the self-fusing material. Further, when two or more vessels are gathered together, the protective member also prevents the vessels from adhering to each other due to contact between the self-fusing material parts. The protective member may be made of any material as long as such purposes can be achieved. For example, a thin film that can be easily broken may be used as the protective member, and the self-fusing material can be covered by attaching the thin film to the surface of the self-fusing material. Specific examples of such a thin film include wafer paper, paper, resin thin films, and metal thin films typified by aluminum foil. Further, the thin film may have a breaking guide line (perforation) so as to be broken at a desired position.

[3. Method for Separating Accommodated Substance in Vessel]

In the present invention, in order to separate the accommodated substance in the vessel, the vessel itself containing the accommodated substance is separated. In the present invention, the vessel is separated through the step (i) of causing fracture in the fracture-inducing portion, the step (ii) of extending the self-fusing material, the step (iii) of separating the accommodated substance, and the step (iv) of separating the first vessel portion and the second vessel portion from each other. The steps of the separation method according to the present invention are schematically shown in FIGS. 3 and 4.

Figure 3:
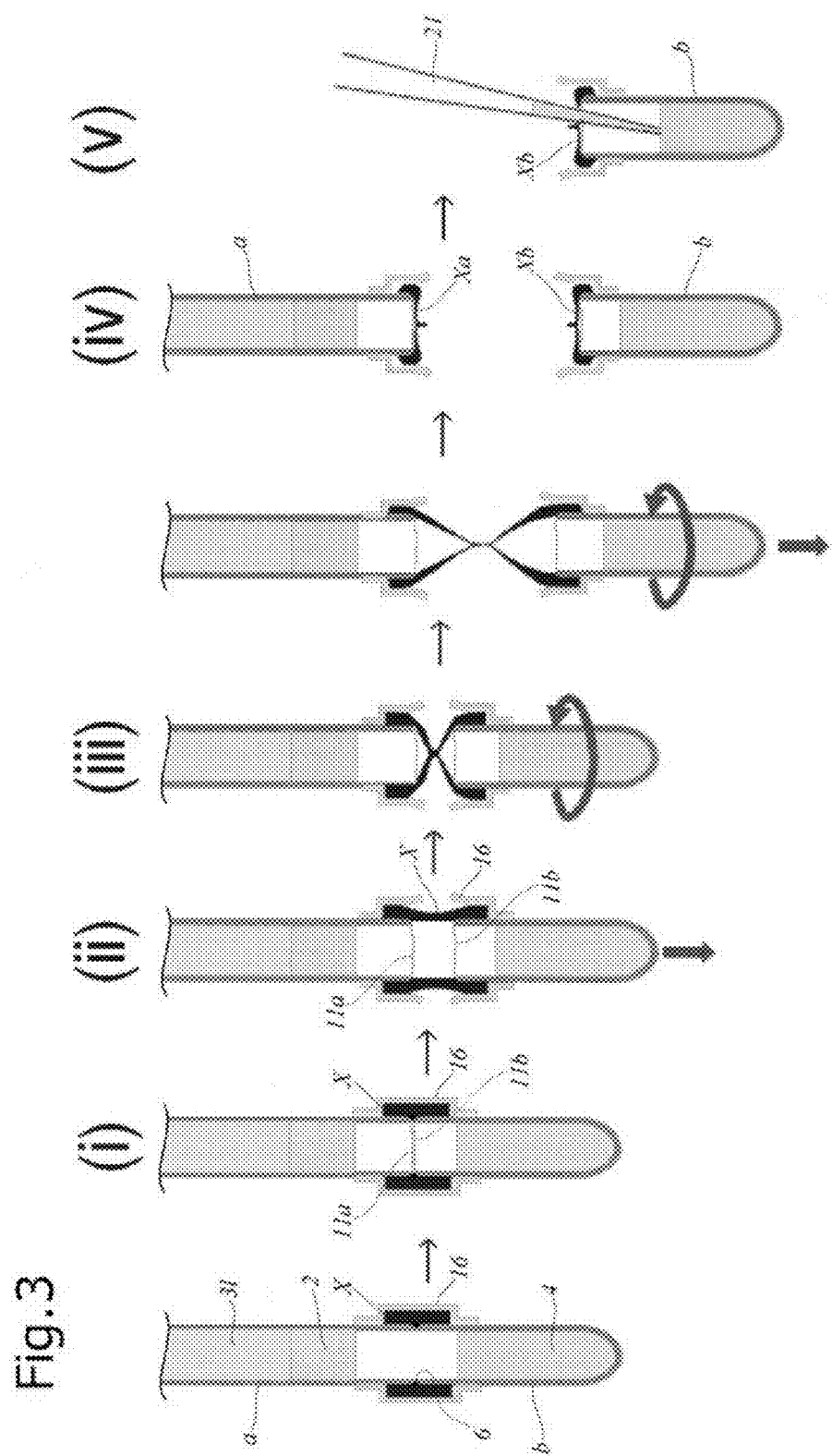
FIG. 3 shows one example of a separation method according to the present invention.
Figure 4:
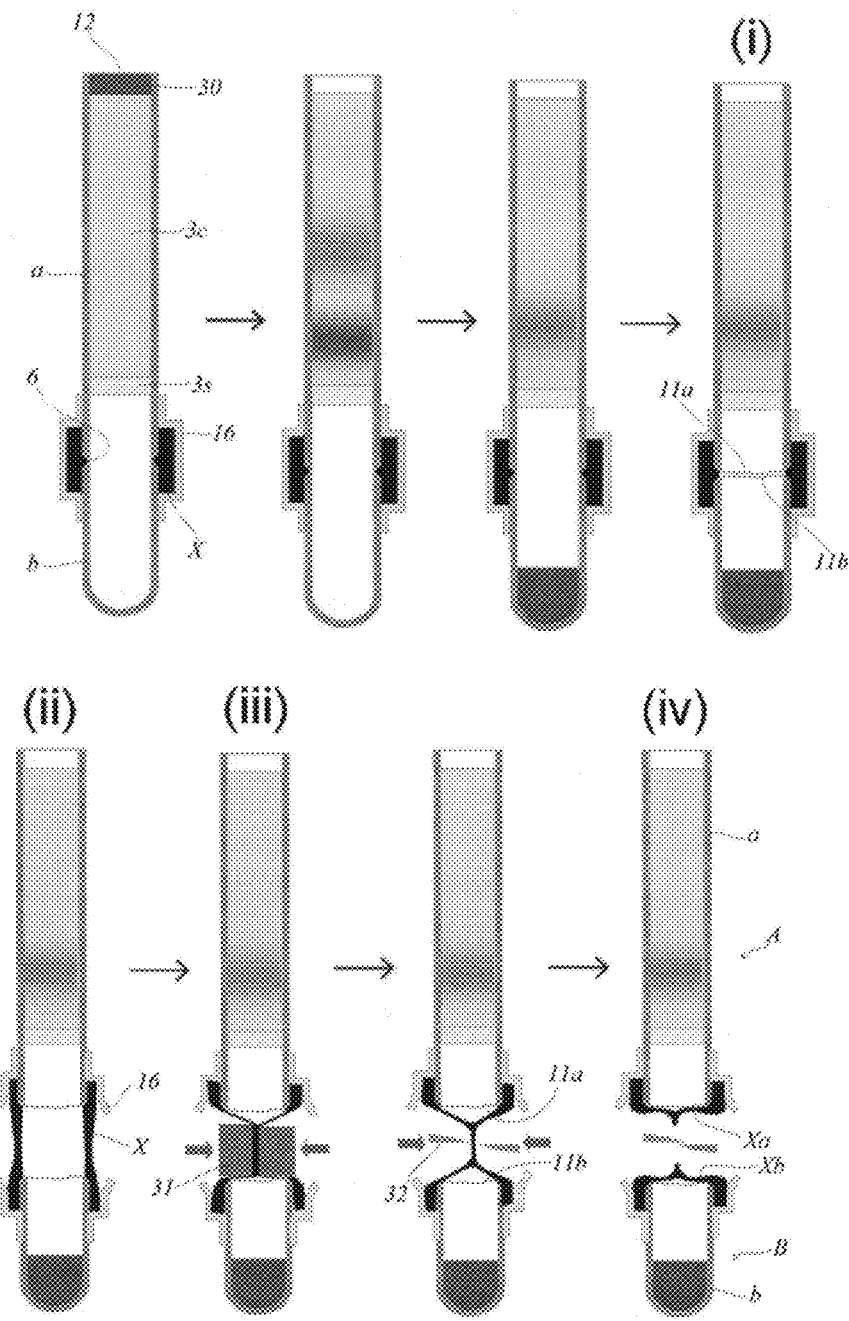
FIG. 4 shows another example of the separation method according to the present invention.

In the step (i), an external force is applied to the vessel to concentrate stress on the fracture-inducing groove 6 so that, as illustrated in FIG. 3 (*i*) or FIG. 4 (*i*), fracture is caused and fracture openings 11a and 11b are formed. The external force shall be such a force that the fracture-inducing groove 6 can be subjected to stress concentration to the extent that fracture occurs. For example, the external force may be a force applied in a direction almost parallel to the fracture-inducing groove 6, a force to pull the first vessel portion and the second vessel portion away from each other, a twisting force around an axis in a direction in which the first vessel portion and the second vessel portion are pulled away from each other, or the resultant of a force to pull the first vessel portion and the second vessel portion away from each other and a twisting force around an axis in a direction in which the first vessel portion and the second vessel portion are pulled away from each other. In the present invention, in consideration of automatically performing the steps for separation, the fracture-inducing portion is preferably fractured by a twisting force. For example, when the steps for separation are automatically performed, a twisting force can be generated by fixing the first vessel portion and the second vessel portion with their respective fixtures (fixtures 91 and 92 of FIG. 9 to be described later) and, without moving one of the fixtures (for example, the fixture fixing the first vessel portion), rotating the other fixture (for example, the fixture fixing the second vessel portion) using rotary means such as a motor. When the vessel has a circular cross-section, a contact surface between the vessel and the fixture may be subjected to anti-slip treatment.

The magnitude of the twisting force is not particularly limited and varies depending on the material of the vessel, the thickness of the vessel, or the type of the fracture-inducing portion (for example, in the case of the fracture-inducing groove, the magnitude of the twisting force varies depending on the depth of the groove, and in other cases, the magnitude of the twisting force varies depending on the material strength of the fracture-inducing portion of the vessel). For example, the magnitude of the twisting force is 8 to 11 cN·m. If the force exceeding the above range is required, there is a tendency that the design of the vessel is less likely to effectively cause stress concentration on the fracture-inducing portion. When the force is less than the above range, there is a tendency that fracture is less likely to effectively occur.

In the step (ii), as illustrated in FIG. 3 (*ii*) and FIG. 4 (*ii*), the first vessel portion a and the second vessel portion b are pulled away from each other to create a sufficient gap between both the vessel portions. The first vessel portion a and the second vessel portion b can be easily pulled away from each other by pulling one of the vessel portions or pulling both the vessel portions in opposite directions. This makes it possible to extend the self-fusing material X. When the self-fusing material X is further covered with the protective member 16, the self-fusing material X is extended and the protective member 16 is torn by pulling both the vessel portions a and b away from each other. The surface having high self-fusibility of the extended self-fusing material X is exposed through a tear in the protective member 16. That is, the surface of the self-fusing material can have high self-fusibility by extending the self-fusing material in the step (ii).

The first vessel portion a and the second vessel portion b are still connected by the self-fusing material X, whereas the self-fusing material X is extended. Therefore, a membrane of the extended self-fusing material X also allows the space in the vessel including the gap created between both the vessel portions a and b to remain completely isolated from an outside atmosphere. The space in the vessel including the gap created between both the vessel portions is separated by the present invention, but a substance allowed to be accommodated in the space as an accommodated substance is not particularly limited, and may be any one selected from the group consisting of a liquid (which may be either aqueous or non-aqueous), a gas and a dispersion system. According to the method of the present invention, it is possible, whatever substance is accommodated in a part to be separated, to separate the substance without leakage to the outside.

It is to be noted that when the temperature of a manipulation environment upon performing the step (ii) is lower than a temperature at which the self-fusing material develops self-fusibility (especially, when a thermoplastic resin is used), appropriate heating may be performed to a temperature at which self-fusion can be achieved.

In the step (iii), the self-fusing material whose surface having high self-fusibility has been exposed by extension is fused together. A method for fusing the self-fusing material is not particularly limited as long as the accommodated substance can be separated by blocking the space between the first vessel portion a and the second vessel portion b so that the interior space of the vessel, which has been a single space so far, is separated.

An example of the method is as follows. As shown in FIG. 3 (*iii*), a twisting force is applied around an axis in a direction in which the first vessel portion a and the second vessel portion b are pulled away from each other. The twisting force may be applied by fixing one of the first vessel portion a and the second vessel portion b and turning the other vessel portion or by turning the first vessel portion a and the second vessel portion b in opposite directions. For example, one or both of the vessel portions a and b may be turned once to twice. This manipulation makes it possible to twist the self-fusing material X, whose surface has high self-fusibility, between both the vessel portions a and b and to self-fuse the self-fusing material X in a twisted state so that the space between the first vessel portion a and the second vessel portion b is completely blocked. As a result, the accommodated substance in the vessel is divided in two.

In the case of this example, the step (ii) and the step (iii) are often performed at the same time. In this case, the self-fusing material can be extended and twisted off by applying, as an external force, the resultant of a twisting force around an axis in a direction in which the first vessel portion a and the second vessel portion b are pulled away from each other and a pulling force in the direction of the axis.

Another example of the method is as follows. As shown in FIG. 4(*iii*), the self-fusing material X, whose surface has high self-fusibility, between the first vessel portion a and the second vessel portion b may also be externally pinched to form a pressure-bonded surface. In this case, in FIG. 4(*iii*), the self-fusing material X whose surface has high self-fusibility is fused together by pressure bonding using two pressure-bonding members 31 so that the space between the first vessel portion a and the second vessel portion b is completely blocked. This makes it possible to divide the accommodated substance in the vessel in two. It is to be noted that an example of pressure-bonding means having two pressure-bonding members 31 as shown in FIG. 4 (*iii*) includes a jig with a pinching function such as a pair of pliers.

In the step (iv), a fused part of the self-fusing material is cut.

In the case of an embodiment shown in FIG. 3, as shown in FIG. 3(*iv*), a self-fused part of the self-fusing material X between both the vessel portions a and b can be twisted off by further twisting (turning) both the vessel portions a and b. In this case, the self-fused part can be easily twisted off by twisting both the vessel portions a and b while further pulling both the vessel portions away from each other.

On the other hand, in the case of an embodiment shown in FIG. 4, as shown in FIG. 4(*iv*), a self-fused part (pressure-bonded surface) of the self-fusing material X between both the vessel portions a and b can be cut using cutting means 32. In this case, the pressure-bonded surface shall be cut at about its center.

In the case of a separation system illustrated in FIG. 4, the cutting means 32 is prepared separately from the pressure-bonding members 31. That is, the cutting means 32 and the pressure-bonding members 31 can be separately used as means and members different in function (either cutting or pressure-bonding), respectively.

Figure 5:
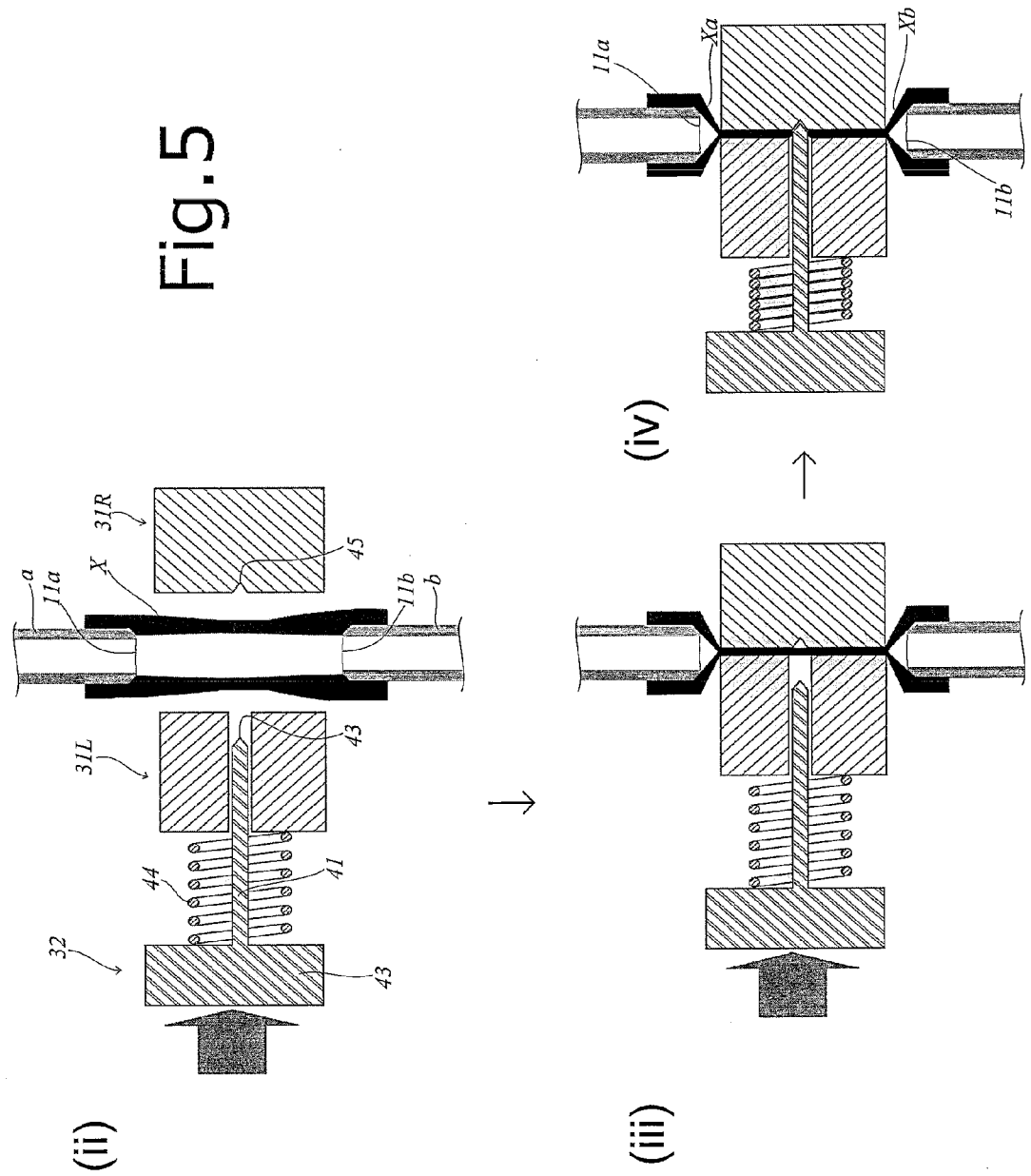
FIG. 5 shows a modified embodiment of a separation system shown in FIG. 4.

On the other hand, as a modified embodiment, the cutting means may be prepared together with the pressure-bonding members so that the separation system has both the functions of cutting and pressure-bonding. A specific example thereof is shown in FIG. 5. The cutting means 32 of a separation system illustrated in FIG. 5 includes a cutter main body 41, whose part including a cutting edge 42 is slidably accommodated in one of the pressure-bonding members 31L, and a pressurizing head 43 provided at the opposite end from the cutting edge 42. A spring 44 is provided between the pressurizing head 43 and the pressure-bonding member 31L. In the other pressure-bonding member 31R, a recess 45 that can receive the cutting edge 42 is provided.

In the case of an embodiment shown in FIG. 5, the self-fusing material X is extended in the step (ii) (FIG. 5(*ii*)), and the extended self-fusing material X is pinched between the pressure-bonding members 31L and 31R by pressing the pressurizing head 32 in the direction of an arrow to form a pressure-bonded surface in the step (iii) (FIG. 5(*iii*)). In the step (iv), the pressurizing head 43 is further pressed so that the cutter main body 41 is slidably moved within the pressure-bonding member 31L, and the cutting edge 42 reaches and cuts the pressure-bonded surface of the self-fusing material X, and then reaches the recess 45 of the pressure-bonding member 31R (FIG. 5(*iv*)).

In the case of the embodiment shown in FIG. 5, unlike the embodiment shown in FIG. 4, the vessel can be separated by the simple operation of only pressing in one direction. Further, the separation system illustrated in FIG. 5 is a simple system by which cutting is performed simply by pressing, and therefore can be miniaturized. Therefore, for example, even when two or more vessels are integrated in series or in a matrix, these structures can be treated collectively by a single action.

In the above cutting step, separated structures can be obtained from the vessel in a state where the fracture openings 11a and 11b are completely closed. Specifically, as shown in FIGS. 3(iv), 4(iv), and 5(iv), a first separated structure is obtained which includes the first vessel portion a, whose fracture opening 11a is closed by a self-fusing material $X_a$, and contains one separated part of the accommodated substance, and a second separated structure is obtained which includes the second vessel portion b, whose fracture opening 11b is hermetically sealed by a self-fusing material $X_b$, and contains the other separated part of the accommodated substance. The fracture openings 11a and 11b, formed by separation, of the respective separated structures are both completely sealed at the same time by a membrane of the extended self-fusing material. That is, leakage or slipping of the accommodated substance does not occur in the separated structure of the first vessel portion a-side, and the accommodated substance in the separated structure of the second vessel portion b-side is completely hermetically sealed.

In this way, part of the vessel can be separated without bringing the accommodated substance to be collected into contact with an outside atmosphere.

As illustrated in FIG. 3(v), the accommodated substance can be reliably taken out from the separated structure without contact with an outside atmosphere or in a safe place by sucking out the accommodated substance through a fine-tipped micropipette chip 21 or an injection needle penetrating a membrane of the self-fusing material $X_b$.

Figure 6:
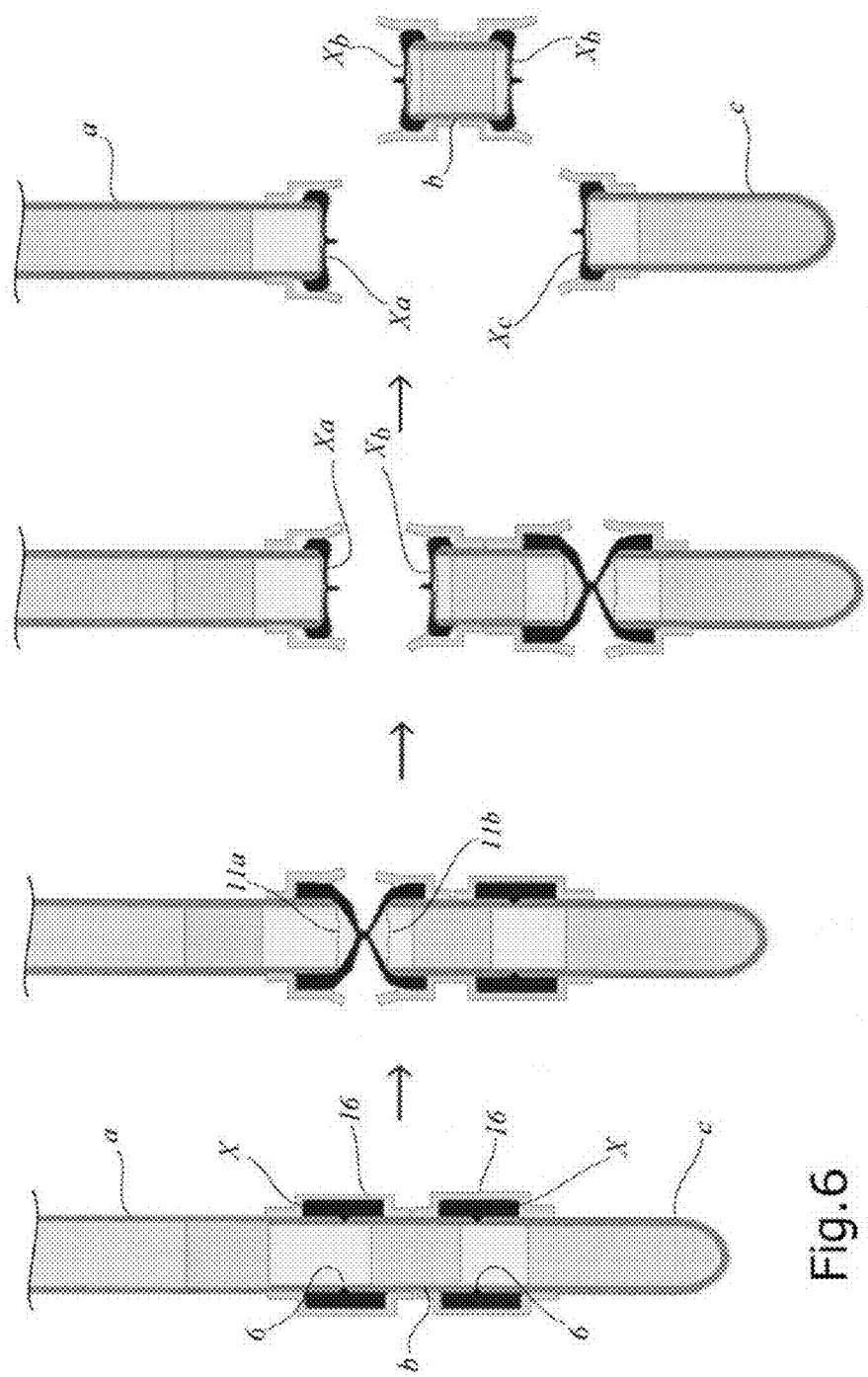
FIG. 6 shows another example of the separation method according to the present invention.

Another modified embodiment of the present invention is shown in FIG. 6. The embodiment shown in FIG. 6 is applied with the embodiment shown in FIG. 4, and is provided with two portions (between a vessel portion a and a vessel portion b and between the vessel portion b and a vessel portion c) to be connected. This makes it possible to collect only a middle part of the vessel (the vessel portion b and a substance accommodated therein). For example, it is possible to take out only a specific band in a column. This embodiment is useful in that a band that becomes undesirably broad as the retention time on a column increases can be fractionated in a sharp state. Similarly, more portions to be connected can also be provided. In the embodiment illustrated in FIG. 6, cutting is performed by the method shown in FIG. 3, but of course, cutting may be performed by the separation system shown in FIG. 4 or 5.

[4. Accommodated Substance in Vessel-Shaped Structure (Manipulation Vessel)]

A substance to be accommodated in the vessel of the present invention is not particularly limited, and one or more are arbitrarily selected from the group consisting of a liquid, a solid, a gas, and a dispersion system.

The liquid may be either an aqueous liquid or a non-aqueous liquid. As for the dispersion system, a dispersion medium and a dispersoid used in combination may each be any one of a solid, a liquid, and a gas. Specific examples of the dispersion system include a gel (which may be either a hydrogel or an oil gel), a sol, and a slurry of a filling material for chromatography and a developing solvent.

The vessel of the present invention may be preferably used to subject an object component to manipulation therein. That is, the vessel of the present invention is used as a manipulation vessel.

In this case, the object component is not particularly limited as long as the object component is a component that can be manipulated in a liquid, a solid, a gas, and a dispersion system. Therefore, the object component may be either a natural product or a non-natural product, and may be either an in-vivo component or an in-vitro component.

A substance to be accommodated in the manipulation vessel includes a manipulation medium as a field for performing manipulation to which an object component is to be subjected. The manipulation of the object component includes subjecting the object component to treatment in the above-described accommodated substance and transporting the object component in the accommodated substance. The treatment to which the object component is to be subjected includes treatment accompanied by a change of the object component into another substance (e.g., chemical reaction and biochemical reaction) and treatment accompanied by a physical change of the object component (e.g., denaturation, dissolution, mixing, emulsification, and dilution of the object component). Processes such as extraction, purification, synthesis, elusion, separation, collection, and analysis of the object component can be performed by these treatments. More specifically, when the object component is, for example, nucleic acid contained in a nucleic acid-containing sample (e.g., tissue, body fluid, excrement), treatments such as nucleic acid extraction, nucleic acid washing, nucleic acid isolation, and a nucleic acid amplification reaction can be performed.

[4-1. Case of Column for Chromatography]

When the manipulation vessel is a column for chromatography (which may have a shape illustrated in FIG. 1(1)), examples of the manipulation medium include a filling material for chromatography and a developing solvent (hereinafter, these may be sometimes simply referred to as a filling material for chromatography). As shown in FIG. 1(1), the filling material for chromatography 3c may be accommodated in the manipulation vessel portion a. Further, a filter 3s may be accommodated so as to be located at the lower end of the filling material for chromatography 3c. The collection vessel portion b may accommodate nothing as shown in FIG. 1(1) or may accommodate a liquid or the like to be mixed with a fraction containing an object component.

Examples of the filling material for chromatography include reverse-phase ODS and a gel filtration carrier, but the filling material for chromatography is not limited thereto and can be appropriately selected by those skilled in the art. The developing solvent and a collection liquid are also appropriately selected by those skilled in the art.

[4-2. Case of Manipulation Tube Device (Capillary Microdevice)]

When the manipulation vessel is a tubular-shaped vessel illustrated in FIG. 1(2), an example of the manipulation medium is a multi-layered object in which layers of an aqueous liquid and a gel are alternately stacked in a longitudinal direction. More specifically, the lowermost layer of the multi-layered object accommodated in the manipulation vessel portion a is usually the gel layer 2, and the liquid layers 31 and the gel layers 3g are alternately stacked on the gel layer 2. An accommodated substance 4 in the collection vessel portion b may be either an aqueous liquid or a gel.

As the aqueous liquid, one required to perform the above-described treatment can be appropriately selected by those skilled in the art. In the above-exemplified case where nucleic acid contained in a nucleic acid-containing sample is an object component to be subjected to treatment, examples of the aqueous liquid include a nucleic acid extraction liquid, a nucleic acid washing liquid, a nucleic acid isolation liquid, and a nucleic acid amplification reaction liquid.

On the other hand, the gel layers sandwich the aqueous liquid in the manipulation tube from both sides in the longitudinal direction of the tube to play a role as a plug (gel plug) fixing the aqueous liquid in a predetermined position in the tube. The gel is comprised of a chemically-inert substance that is insoluble or poorly-soluble in a liquid constituting the aqueous liquid layer when stacked together with the aqueous liquid in the tube. The phrase "insoluble or poorly-soluble in a liquid" means that the degree of solubility in the liquid at 25° C. is about 100 ppm or less.

The gel includes both an organogel and a hydrogel.

As the organogel, one prepared by gelling a water-insoluble or poorly water-soluble liquid substance with the addition of a gelling agent may be usually used. As the water-insoluble or poorly water-soluble liquid substance, an oil is used, whose degree of solubility in water at 25° C. is about 100 ppm or less and which is in a liquid state at ordinary temperature (25° C.±15° C.). For example, one or a combination of two or more selected from the group consisting of liquid oils and fats, ester oils, hydrocarbon oils, and silicone oils may be used. As the gelling agent, one or a combination of two or more oil-gelling agents selected from the group consisting of hydroxy fatty acids, dextrin fatty acid esters, and glycerin fatty acid esters may be used. The amount of the gelling agent added to the liquid substance may be, for example, 0.1 to 0.5 wt %, 0.5 to 2 wt %, or 1 to 5 wt % of the total weight of the liquid substance. A gelling method can be appropriately determined by those skilled in the art.

As the hydrogel, one prepared by equilibrium swelling of a hydrogel material in water or an aqueous liquid may be used. Examples of the hydrogel material include gelatin, collagen, starch, pectin, hyaluronic acid, chitin, chitosan, alginic acid, and derivatives thereof.

As in the case of the above-described aqueous liquid, when the hydrogel is one that provides an environment for treatment to which an object component is to be subjected (as one example, the hydrogel is a DNA hydrogel (P-gel) that provides a reaction environment for obtaining a protein from an object component when the object component is a substrate for protein synthesis), such a hydrogel is appropriately prepared by those skilled in the art so as to have composition suitable for such treatment.

The multi-layered object may be accommodated in at least the manipulation vessel portion a. As will be described later, the aqueous liquid forming an uppermost layer may further contain magnetic particles. In the collection vessel portion b, a substance suitable for collecting an object component (which is selected from the group consisting of a liquid, a solid, a gas, and a dispersion system) is accommodated.

The rough inner diameter of a tube constituting the manipulation tube is, for example, 0.1 mm to 5 mm, preferably 1 to 2 mm from the viewpoint of ensuring excellent manipulability, but is not limited thereto. The length in longitudinal direction of the tube is, for example, 1 to 30 cm, preferably 5 to 15 cm. The multi-layered object is accommodated in the tube having such sizes by forming a desired number of layers in a manner that gel plugs having a thickness of, for example, 1 to 20 mm, preferably 2 to 5 mm are contained.

[4-3. Case of Droplet Manipulation Device]

When the manipulation vessel has a shape illustrated in FIG. 2, an aqueous liquid added thereto is sunk as the droplet $3d$ in the droplet encapsulating medium 5, and accommodated in the vessel, if the specific gravity of the droplet encapsulating medium 5 in which a sol-gel transition function is given to the above-described water-insoluble or poorly water-soluble liquid substance is less than 1. The droplet can be made movable or immovable by controlling the temperature of the droplet encapsulating medium 5 with the use of its sol-gel transition temperature as a border. Further, a recess may be formed in the surface of the gel-state droplet encapsulating medium to hold the droplet $3d'$ of an aqueous liquid in the recess.

The amount of the aqueous liquid constituting one droplet $3d$ accommodated in the vessel is not particularly limited, but is, for example, about 0.1 to 20 µL.

The amount of the droplet encapsulating medium 5 accommodated in the vessel is not particularly limited as long as the amount is sufficient to completely encapsulate the droplet $3d$. Specifically, the droplet encapsulating medium, whose volume is 1,0 times to 10,000 times, or 1,000 times to 50,000 times that of the droplet, can be used.

As will be described later, the aqueous droplet $3d'$ accommodated in the vessel may further contain magnetic particles.

[5. Example of Use of Device Using Manipulation Vessel]

[5-1. Case of Column for Chromatography]

As shown in FIG. 4, an impurity-containing object substance sample liquid 30 charged through the sample supply portion 12 is fractionated by the filling material for chromatography $3c$ in the manipulation portion A, and a fraction of an object component is filtered through the filter $3s$ and a filtrate is dropped into the collection portion B. A hermetically-sealed air layer is present between the filter $3s$ and the collection liquid 4, and therefore after the filtrate is dropped into the collection portion to some extent, the amount thereof is stopped at a predetermined level due to an increase in the internal pressure of the collection portion B. (If the manipulation portion A and the collection portion B are separated from each other not by the method according to the present invention, a filtrate immediately starts to drop again from the filter due to atmospheric pressure. If the filtrate is derived from a fraction containing impurities, the impurities flow into the collection portion B.)

Then, as shown in FIGS. 4(i) to 4(iv), the filtrate can be collected by separating the collection portion B from the column by the method according to the present invention.

[5-2. Case of Manipulation Vessel Using Magnetic Particles]

Hereinbelow, a device using a manipulation tube as the manipulation vessel (capillary microdevice) and a device using a rectangular (or deformed rectangular) vessel as the manipulation vessel (droplet manipulation device) will be described. In each of the devices, manipulation such as capture or transport of an object component can be performed by adsorbing the object component to magnetic particles and fluctuating a magnetic field from the outside of the manipulation vessel with the use of magnetic field applying means.

Figure 7:
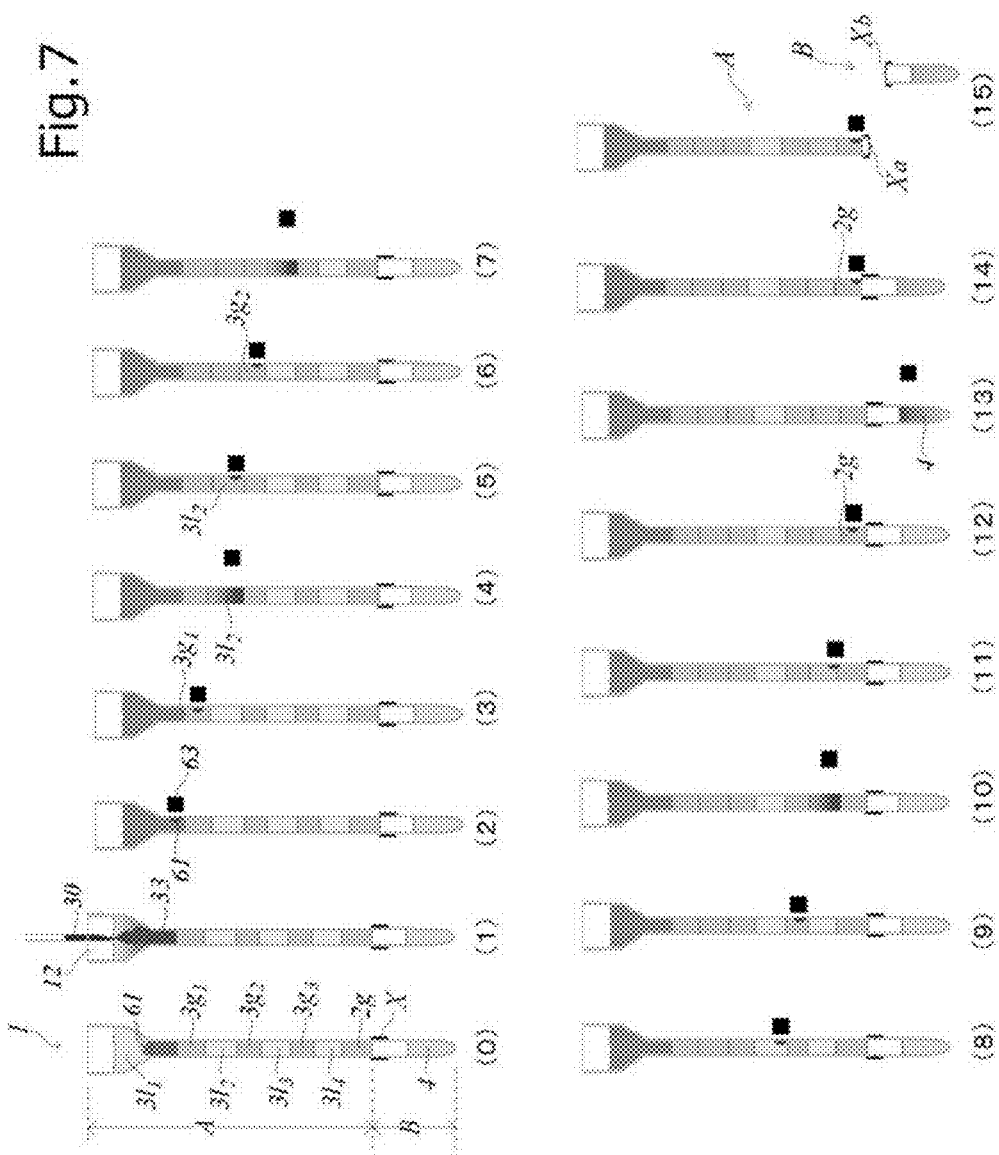
FIG. 7 shows an example of performing the method according to the present invention with the use of a device using a manipulation tube.
Figure 8:
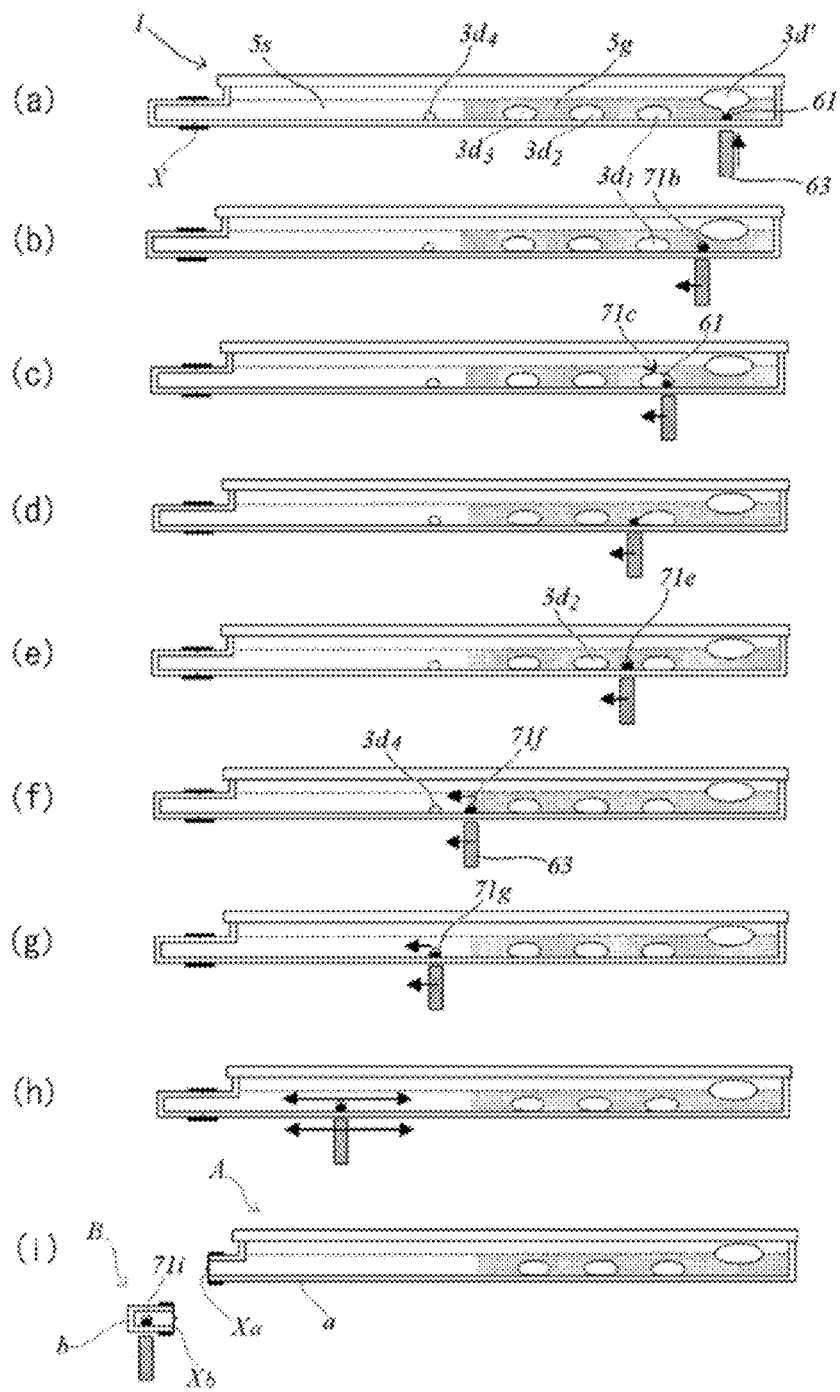
FIG. 8 shows an example of performing the method according to the present invention with the use of a device using a plate-shaped vessel.

The magnetic particles are used to move an object component in the manipulation vessel together with a small amount of liquid lump to be accompanied by moving a magnetic field from the outside of the manipulation vessel. The magnetic particles usually have a chemical functional group on the surface thereof. The magnetic particles may be accommodated in the manipulation vessel in advance, or may not be accommodated in the manipulation vessel in advance. When the magnetic particles are accommodated in the manipulation vessel in advance, for example, magnetic particles 61 may be previously contained in an uppermost aqueous liquid layer $3g_1$ as shown in FIG. 7, or may be previously contained in an aqueous liquid present nearest the sample supply portion, such as an aqueous droplet $3d'$ placed on a droplet encapsulating medium $5g$, as shown in FIG. 8.

On the other hand, when not accommodated in the manipulation vessel in advance, the magnetic particles are supplied into the manipulation vessel in the state of being mixed with a sample containing an object component.

The magnetic particles are not particularly limited as long as they are particles that respond to magnetism. Examples thereof include particles having a magnetic material such as magnetite, γ-iron oxide, or manganese zinc ferrite. Further, the magnetic particles may have a surface having a chemical structure specifically binding to a target component to be subjected to the above-described treatment or reaction, such as an amino group, a carboxyl group, an epoxy group, avidin, biotin, digoxigenin, protein A, protein G, a complexed metal ion, or an antibody or may have a surface specifically binding to a target component by electrostatic force or van der Waals force. This makes it possible to selectively adsorb a target component to be subjected to reaction or treatment to the magnetic particles.

Examples of a hydrophilic group on the surface of the magnetic particles include a hydroxyl group, an amino group, a carboxyl group, a phosphoric group, and a sulfonic group.

The magnetic particles may further contain, in addition to the above elements, various elements appropriately selected by those skilled in the art. Preferred specific modes of the magnetic particles having a hydrophilic group on their surface include particles composed of a mixture of a magnetic material and silica and/or an anion exchange resin, magnetic particles whose surfaces are coated with silica and/or an anion exchange resin, magnetic particles whose surfaces are coated with gold having a hydrophilic group binding thereto through a mercapto group, and gold particles containing a magnetic material and having a hydrophilic group binding to their surface through a mercapto group.

The average particle size of the magnetic particles having a hydrophilic group on their surface may be about 0.1 μm to 500 μm. When the average particle size is small, the magnetic particles are likely to be present in a dispersed state in the aqueous liquid layer when freed from a magnetic field.

The magnetic field applying means that causes the movement of a magnetic field for moving the magnetic particles in the manipulation vessel together with an object component is not particularly limited. As the magnetic field applying means, a magnetic force source such as a permanent magnet (e.g., a ferrite magnet or a neodymium magnet) or an electromagnet can be used. The magnetic field applying means can be arranged outside of and close to the manipulation vessel to the extent that the magnetic particles dispersed in the aqueous liquid layer or droplet in the manipulation vessel can be aggregated on the inner wall surface (transfer surface) of the manipulation vessel, and that the aggregated magnetic particles in the gel layer or droplet encapsulating medium in the manipulation vessel can be transported while remaining in an aggregation state. This makes it possible for the magnetic field applying means to effectively produce a magnetic field for the magnetic particles in a state where the transfer surface of the manipulation vessel is interposed between the magnetic particles and the magnetic field applying means, thereby allowing an object component to be captured and transported together with the aggregated magnetic particles.

Further, the magnetic particles can be moved even in a gel by externally operating a magnetic field, and therefore can pass through the gel. This is due to the thixotropic properties (thixotropy) of the gel. That is, the magnetic particles in the manipulation vessel give a shear force to the gel along the transfer surface by externally moving a magnet, and the gel in front of the magnetic particles in the direction in which the magnetic particles are moved is fluidized by solation so that the magnetic particles can be moved directly. Further, after the passage of the magnetic particles, the sol freed from the shear force is immediately returned to a gel state, and therefore a through hole is not formed in the gel by the passage of the magnetic particles. By utilizing such a phenomenon, an object substance can be easily moved using magnetic particles as a carrier, and therefore, for example, it is possible to perform switching among various chemical environments to which the object substance is to be subjected and which is created by droplets in a very short time.

[5-2-1. Case of Manipulation Tube Device (Capillary Microdevice)]

As an example of use of a manipulation tube, a method (FIG. 7) will be described below, in which nucleic acid is extracted from a biological sample containing nucleic acid as an object component, and washed in a manipulation tube. Means for subjecting an object component other than nucleic acid to a desired manipulation can be appropriately selected by those skilled in the art with reference to the following example.

In a manipulation tube shown in FIG. 7, a multi-layered object, in which a cell lysis liquid (containing a surfactant and a chaotropic salt such as guanidine thiocyanate) $31_1$ and washing liquids $31_2$ to $31_4$ and gel plugs $3g_1$ to $3g_3$ and $2g$ are alternately stacked, is accommodated in a manipulation vessel portion a, and an eluent 4 is accommodated in a collection vessel portion b with an air layer interposed between the multi-layered object and the eluent 4.

In a manipulation portion A, a biological sample 30 containing an object component is supplied to the cell lysis liquid $31_1$ in the manipulation tube 1 through a sample supply portion 12 so that nucleic acid is isolated from cells (FIG. 7(1)). The isolated nucleic acid can be specifically adsorbed to the silica surface of magnetic particles 61. The adsorbed nucleic acid is accompanied by reaction-inhibiting components as it is, and therefore cannot be directly used as a template for gene amplification reaction. For this reason, the magnetic particles are washed with the washing liquid $31_2$ while the nucleic acid remains adsorbed to the surface of the magnetic particles. At this time, in order to prevent a large amount of the reaction-inhibiting components from being brought into the washing liquid, the magnetic particles 61 are gathered by a magnet 63 (FIG. 7(2)) and are allowed to pass through the gel plug $3g_1$ separating the cell lysis liquid $31_1$ and the washing liquid $31_2$ from each other (FIG. 7(3)). By allowing the magnetic particles to pass through the gel plug $3g_1$, the magnetic particles can reach the washing liquid $31_2$ together with few liquid fractions (FIG. 7(4)). Therefore, the magnetic particles can be highly efficiently washed. Further, by repeating the passage of the magnetic particles through the gel plug ($3g_2$, $3g_3$) and the transport of the magnetic particles to the washing liquid ($31_3$, $31_4$) (FIGS. 7(5) to 7(10)), the degree of purification of the nucleic acid can be increased. The nucleic acid purified while remaining adsorbed to the surface of the magnetic particles is again gathered by the magnet (FIG. 7(11)), allowed to pass through the gel plug $2g$ (FIG. 7(12)), and transported into the eluent 4 (FIG. 7(13)). In the eluent 4, the nucleic acid is separated from the magnetic particles and eluted. When contamination of the magnetic particles into a collected substance is not desired, for example, the magnetic particles, from which the nucleic acid has been eluted, are again stayed in the gel plug $2g$, and the eluted purified nucleic acid remains in the collection portion B (FIG. 7(14)). The thus obtained nucleic acid is useful as template nucleic acid that can be analyzed by a nucleic acid amplification reaction. The obtained nucleic acid can be collected in a completely hermetically-sealed state by detaching the collection portion B from the manipulation portion A of the manipulation tube by the separation method according to the present invention (FIG. 7(15)). The collected nucleic acid can be subjected to the next manipulation (process of performing analysis by a nucleic acid amplification reaction).

In a modified embodiment of the above embodiment, any one of the accommodated substances in the manipulation tube (e.g., the washing liquid $31_4$ or the eluent 4) may be changed to a nucleic acid amplification liquid. In this case, the extracted and washed nucleic acid can be amplified by subjecting the nucleic acid amplification liquid to appropriate temperature cycles with the use of appropriate heating means. The amplified nucleic acid can be collected in a completely hermetically-sealed state by detaching the collection portion B from the manipulation portion A by the separation method according to the present invention.

[5-2-2. Case of Droplet Manipulation Device]

As an example of a droplet manipulation device, a method (FIG. 8) will be described below, in which nucleic acid is extracted from a biological sample containing nucleic acid as an object component, washed, and amplified in a manipulation tube. Means for subjecting an object component other than nucleic acid to a desired manipulation can be appropriately selected by those skilled in the art with reference to the following example.

A device shown in FIG. 8 can be prepared in the following manner. A heated mixture (e.g., 90° C.) of, for example, a silicone oil and an oil-gelling agent is filled into a vessel to have a filling height of, for example, about 3 mm. After the temperature of the heated mixture is reduced (e.g., 60° C.) one droplet $3d_1$ of a nucleic acid extraction liquid, two droplets $3d_2$ and $3d_2$ of a washing liquid, and one droplet $3d_4$ of a PCR reaction liquid are placed in the oil, and the oil is allowed to stand until its temperature is reduced to room temperature so that the entire oil can be gelled. Further, a recess can be formed in the surface of the gelled oil to place a mixture $3d'$ of a cell lysis liquid containing magnetic silica particles and a nucleic acid-containing biological sample in the recess.

After the vessel is covered, the end of an alumina ceramic plate (not shown) is separately heated with an electric heater. At the time when a temperature gradient is stably created on the surface of the plate, the vessel is placed on the plate and allowed to stand. In this way, part (left half in FIG. 8) of the gel in the vessel is solated by heat, and therefore both a gel 5g having no fluidity and a sol 5s having fluidity coexist as a droplet encapsulating medium.

As shown in FIG. 8(*a*), since the droplet encapsulating medium 5g is in a gel state having no fluidity, the magnetic particles 61 can be separated toward a transfer surface direction by bringing the magnetic force source (magnet) 63 close to the vessel 1 to generate a magnetic field in a direction from the transfer surface side toward the droplet $3d'$ on the droplet encapsulating medium 5g, while the droplet $3d'$ remains placed on the droplet encapsulating medium 5g. At this time, the magnetic particles 61 to be separated form an aggregate by a magnetic force, and the aggregated magnetic particle group accompanies a substance adsorbed thereto and a small amount of liquid adhered around thereto. In other words, when the droplet $3d'$ is regarded as a main droplet, a small droplet 71*b* containing the magnetic particles is separated. The separated small droplet 71*b* is moved through the droplet encapsulating medium 5g while breaking the tertiary structure of the gel under the guidance of a magnetic field, and therefore can be sunk to the transfer surface of the vessel.

As shown in FIG. 8(*b*), the small droplet 71*b* containing the magnetic particles and nucleic acid and other components attached thereto is moved through the droplet encapsulating medium 5g, and coalesced with another encapsulated droplet $3d_1$ comprised of a nucleic acid extraction liquid (FIG. 8(*c*)), which makes it possible to extract a nucleic acid component contained in the small droplet 71*b*. Further, as shown in FIGS. 8(*d*) and 8(*e*), the extracted nucleic acid, which is accompanied with the magnetic particles together with a small droplet 71*e*, is separated from an encapsulated droplet 71*c* comprised of the nucleic acid extraction liquid coalesced with the small droplet 71*b*, and is moved into the droplet encapsulating medium 5g by fluctuating a magnetic field.

Similarly in the case of performing washing treatment, the magnetic particles can be washed by moving the small droplet 11*e* through the encapsulating medium 5g and coalescing the small droplet with the encapsulated droplet $3d_2$ comprised of a washing liquid. By washing the magnetic particles, the nucleic acid adsorbed to the magnetic particles can be washed. Further, the washed nucleic acid, which is accompanied with the magnetic particles together with a small droplet, is separated from the encapsulated droplet comprised of a washing liquid, and is moved into the encapsulating medium by fluctuating a magnetic field. Similarly, the magnetic particles can be washed again by coalescing the small droplet with another encapsulated droplet $3d_3$ comprised of a washing liquid.

The nucleic acid-containing sample or a small droplet 71*f* subjected to the above-described nucleic acid extraction treatment and washing treatment, if necessary, is coalesced with the droplet $3d_4$ comprised of a nucleic acid amplification liquid (FIGS. 8 (*f*) and 8 (*g*)). This makes it possible to obtain a droplet 71*g* comprised of the nucleic acid amplification liquid containing the nucleic acid to be amplified and the magnetic particles. The droplet encapsulating medium 5s surrounding the droplet $3d_4$ is in a sol state having fluidity, and therefore the entire droplet 71*g* obtained by coalescence with the droplet 71*f* can be moved. A nucleic acid amplification reaction can be started by moving the droplet 71*g* to a point of a nucleic acid amplification reaction initiation temperature in a temperature variable region (FIG. 8 (*h*)).

After the completion of the nucleic acid amplification reaction, as shown in FIG. 8(*i*), a droplet 71*l* containing an amplified product is moved into the collection portion B, and the amplified product can be collected in a completely hermetically-sealed state by detaching the collection portion B from the manipulation portion A by the separation method according to the present invention.

EXAMPLES

Experimental Example 1

Figure 9:
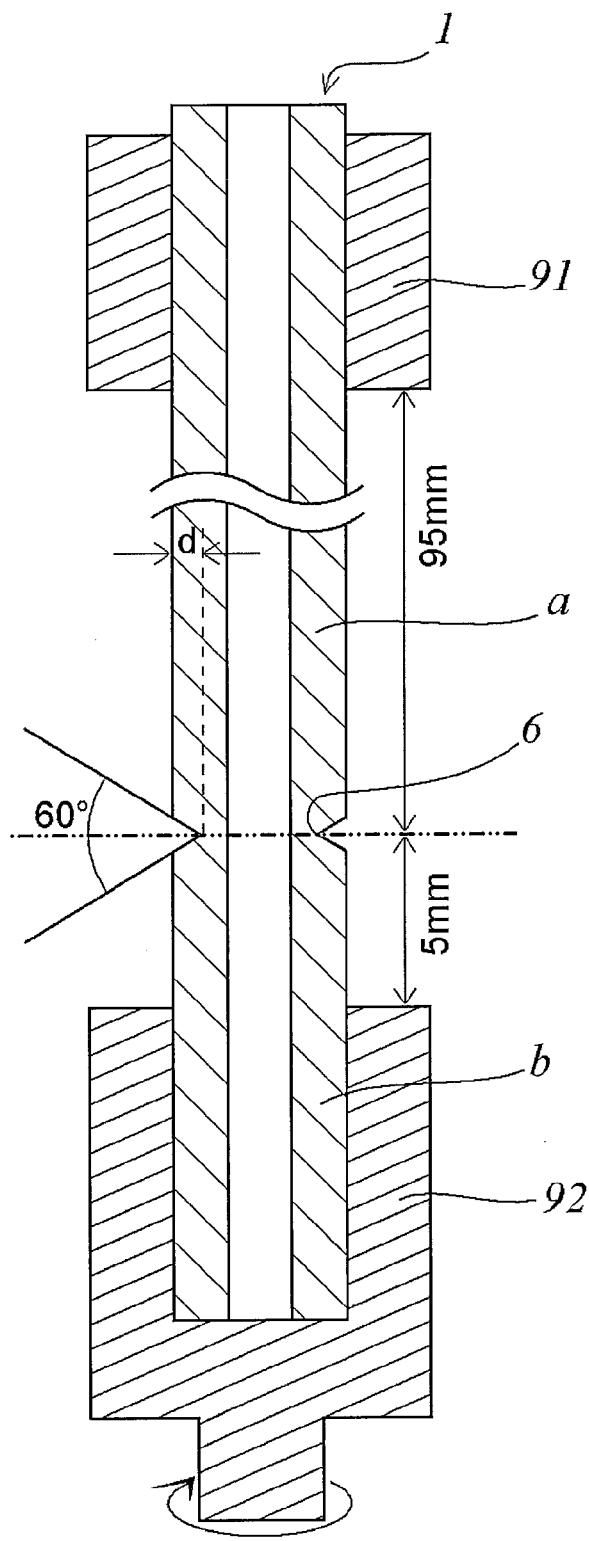
FIG. 9 is a vertical sectional view of a vessel tested in Experimental Example 1.

A vessel 1 shown in FIG. 9 was prepared. Specifically, a fracture-inducing groove 6 was formed by notching a polypropylene capillary (outer diameter: 4 mm, inner diameter: 2 mm) in a position where the capillary should be separated (position where fracture should be caused). The fracture-inducing groove was formed to have a cross section having a V shape with an angle of 60° and a depth of d. A vessel portion a of the vessel 1 was fixed by a fixture 91, and a vessel portion b was fixed by a fixture 92. At this time, the fixation was performed in such a manner that the length from the lower end of the fixture 91 to the deepest point of the fracture-inducing groove 6 was 95 mm, and the length from the upper end of the fixture 92 to the deepest point of the fracture-inducing groove 6 was 5 mm. The fixture 91 was fixed so as not to turn. On the other hand, the fixture 92 was connected to a motor, and a rotational torque was applied to the fixture 92 to cause fracture in the fracture-inducing groove 6. As a result, the vessel 1 was separated into the vessel portion a and the vessel portion b.

Figure 10:
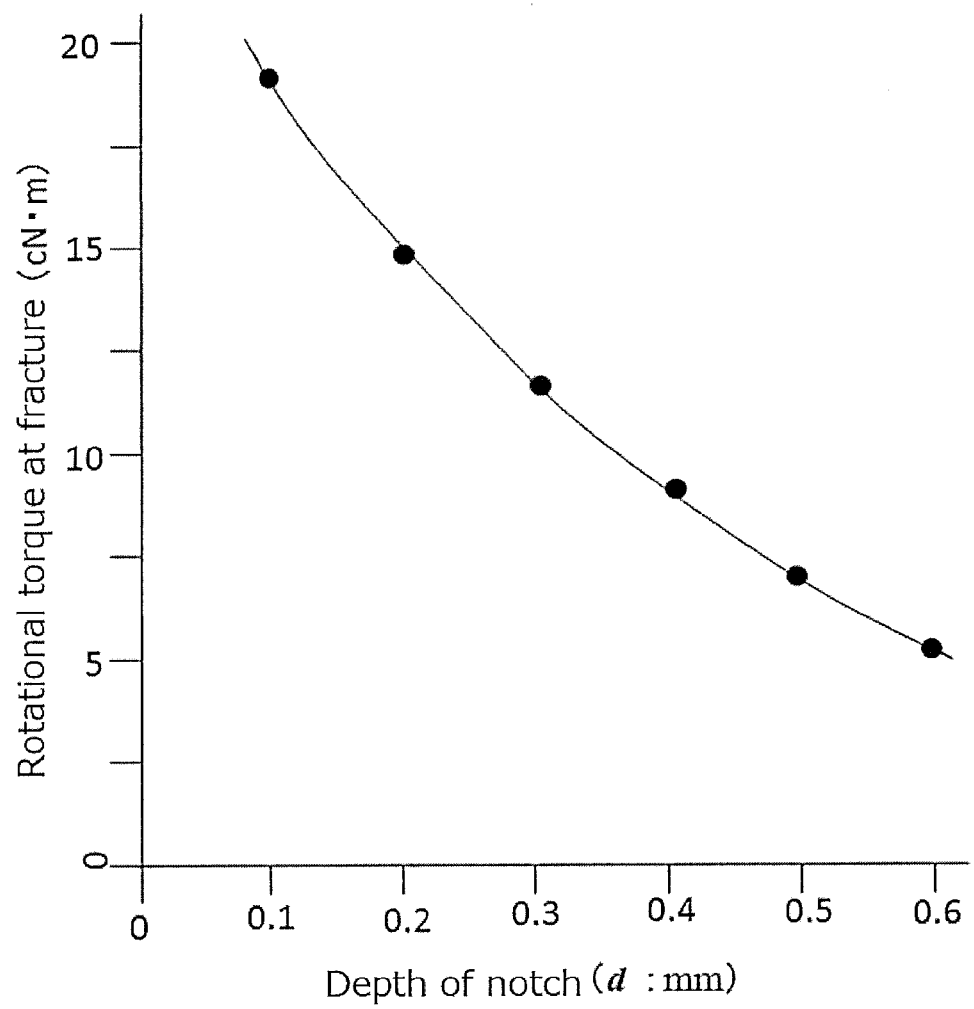
FIG. 10 is a graph showing a relationship between the depth of a fracture-inducing groove and a rotational torque that causes a vessel to be separated due to stress concentration on the fracture-inducing groove.

A relationship between the depth d of the fracture-inducing groove and the rotational torque causing the capillary to be separated due to stress concentration on the fracture-inducing groove is shown in FIG. 10. As can be seen from the results, conditions such that fracture in the fracture-inducing groove due to stress concentration is caused when a rotational torque of 8 to 11 cN·m is applied at a depth of 0.3 to 0.5 mm are particularly suitable in this experimental example. The above ranges are optimal ranges in which the toughness of the capillary as a vessel device is not impaired and fracture cannot be easily caused manually but fracture and separation can be mechanically caused with high reproducibility.

Experimental Example 2

A fracture-inducing zone was formed in a polypropylene capillary (outer diameter: 4 mm, inner diameter: 2 mm) in a position where the capillary should be separated (position where fracture should be caused) in the following manner. Seventy percent (v/v) concentrated nitric acid was applied with a width of 2 mm onto the outer peripheral surface of the capillary in a position where the capillary should be separated, and was then heated at 70° C. for 1 hour to denature polypropylene from the application surface toward the inside of a vessel wall. The manipulation of applying and heating concentrated nitric acid was repeated until yellowing due to denaturation finally reached the midpoint of the vessel wall in the thickness direction thereof.

The fracture-inducing zone was washed, and was then wrapped and covered with butyl rubber. In this way, a separable vessel was prepared.

The invention claimed is:

1. A separable vessel comprising:
   a fracture-inducing portion formed in a position where fracture should be caused to separate the vessel into a first vessel portion and a second vessel portion; and
   a self-fusing material provided on an outer surface so as to cover the fracture-inducing portion,
   wherein the fracture-inducing portion has a reduced wall thickness and/or a reduced material strength as compared with the rest of the vessel.

2. The vessel according to claim 1, containing an accommodated substance therein.

3. The vessel according to claim 2, being a manipulation vessel for subjecting a sample containing an object component to a predetermined manipulation therein, wherein
   the first vessel portion is a manipulation portion for subjecting a sample containing an object component to a predetermined manipulation,
   the second vessel portion is a collection portion for collecting a target substance from the manipulation portion, and
   the accommodated substance is a manipulation medium selected from the group consisting of a liquid, a solid, a gas, and a dispersion system, as a field for performing manipulation to which the object component is to be subjected.

4. The vessel according to claim 3, wherein the manipulation portion comprises a column for chromatography, and the manipulation medium comprises a filling material for chromatography and a developing solvent.

5. The vessel according to claim 3, having a tubular shape, wherein the manipulation medium is a multi-layered object in which layers of an aqueous liquid and a gel are alternately stacked in a longitudinal direction.

6. The vessel according to claim 3, wherein the manipulation medium comprises a droplet encapsulating medium and an encapsulated aqueous droplet.

7. The vessel according to claim 1, further comprising a protective member on an outer surface of the self-fusing material.

8. The vessel according to claim 1, wherein the self-fusing material has a thickness of 0.01 to 5 mm per 1 $cm^2$ of area of a plane within an outer periphery of the vessel.

9. The vessel according to claim 1, wherein the self-fusing material is selected from the group consisting of isobutylene-isoprene copolymers, ethylene-propylene-diene copolymers, polyisobutylene, paraffin, polyvinyl acetate, polyurethane, polydimethyl siloxane, ethylene propylene copolymers, hydrogel polymers, (meth)acrylic acid ester copolymers, silicone rubber, and natural rubber.

10. The vessel according to claim 1, wherein the self-fusing material is a thermoplastic resin having a glass transition temperature of 50°C. to 180°C.

11. The vessel according to claim 10, wherein the thermoplastic resin is selected from the group consisting of polyethylene, polypropylene, polystyrene, ethylene-vinyl acetate copolymers, polyacetal, polymethyl methacrylate, polyvinyl alcohol, polyvinyl chloride, vinyl chloride-vinyl acetate copolymers, vinyl chloride-acrylic acid ester copolymers, polyvinylidene chloride, and vinylidene chloride-acrylic acid ester copolymers.

12. A manipulation device for manipulating an object component in a vessel, comprising:
    the vessel according to claim 2;
    magnetic particles that should capture and transport an object component; and
    a magnetic field application member for applying a magnetic field to the vessel so that the magnetic particles can be moved from an inside of the first vessel portion to an inside of the second vessel portion.

13. A method for separating a substance accommodated in a vessel, the vessel being a separable vessel comprising: a fracture-inducing portion formed in a position where fracture should be caused to separate the vessel into a first vessel portion and a second vessel portion; and a self-fusing material provided on an outer surface so as to cover the fracture-inducing portion, wherein the fracture-inducing portion has a reduced wall thickness and/or a reduced material strength as compared with the rest of the vessel, and the vessel contains an accommodated substance therein,
    the method comprising subjecting the vessel to the following steps:
    (i) applying an external force to the vessel to cause fracture in a position of the fracture-inducing portion so that the first vessel portion and the second vessel portion are separated from each other to form fracture openings of the respective vessel portions but are connected to each other through the self-fusing material;

(ii) pulling the first vessel portion and the second vessel portion away from each other to extend the self-fusing material;

(iii) fusing the extended self-fusing material together so that a space between the first vessel portion and the second vessel portion is blocked to separate the accommodated substance; and (iv) cutting a fused part of the self-fusing material to separate the vessel into a first separated structure that includes the first vessel portion whose fracture opening is closed by the self-fusing material and that contains one of the separated parts of the accommodated substance, and a second separated structure that includes the second vessel portion whose fracture opening is closed by the self-fusing material and that contains the other separated part of the accommodated substance.

14. The method according to claim 13, wherein the external force in the step (i) is a twisting force around an axis in a direction in which the first vessel portion and the second vessel portion are to be pulled away from each other in the step (ii).

15. The method according to claim 14, wherein the twisting force is 8 to 11 cN·m.

16. The method according to claim 13, wherein in the steps (iii) and (iv), the fusion of the extended self-fusing material together and the cutting of the fused part are performed by twisting the first vessel portion and the second vessel portion around an axis in a direction in which the first vessel portion and the second vessel portion have been pulled away from each other.

17. The method according to claim 13, wherein the extended self-fusing material is fused together by externally pinching with a pressure-bonding member in the step (iii), and the fused part is cut with a cutting member in the step (iv).

18. The method according to claim 17, wherein the pressure-bonding member and the cutting member are separately prepared.

19. The method according to claim 17, wherein the pressure-bonding member comprises a pair of pressure-bonding members; and the cutting member is prepared in such a manner that a flat plate-shaped cutting blade is provided so as to be able to penetrate into one member of the pair of pressure-bonding members, and the cutting of the fused part in the step (iv) is performed by allowing the flat plate-shaped cutting blade to penetrate the one of the pair of pressure-bonding members.

20. The method according to claim 13, wherein the vessel to be subjected to the steps (i) to (iv) further comprises a protective member on an outer surface of the self-fusing material.

21. The method according to claim 13, wherein the self-fusing material has a thickness of 0.01 to 5 mm per 1 cm$^2$ of area of a plane within an outer periphery of the vessel.

22. The method according to claim 13, wherein the self-fusing material is selected from the group consisting of isobutylene-isoprene copolymers, ethylene-propylene-diene copolymers, polyisobutylene, paraffin, polyvinyl acetate, polyurethane, polydimethyl siloxane, ethylene propylene copolymers, hydrogel polymers, (meth)acrylic acid ester copolymers, silicone rubber, and natural rubber.

23. The method according to claim 13, wherein the self-fusing material is a thermoplastic resin having a glass transition temperature of 50°C. to 180°C.

24. The method according to claim 23, wherein the thermoplastic resin is selected from the group consisting of polyethylene, polypropylene, polystyrene, ethylene vinyl acetate copolymers, polyacetal, polymethyl methacrylate, polyvinyl alcohol, polyvinyl chloride, vinyl chloride-vinyl acetate copolymers, vinyl chloride-acrylic acid ester copolymers, polyvinylidene chloride, and vinylidene chloride-acrylic acid ester copolymers.

25. The method according to claim 13, wherein the vessel is a manipulation vessel for subjecting a sample containing an object component to a predetermined manipulation therein, the first vessel portion is a manipulation portion for subjecting a sample containing an object component to a predetermined manipulation, the second vessel portion is a collection portion for collecting a target substance from the manipulation portion, and the accommodated substance is a manipulation medium selected from the group consisting of a liquid, a solid, a gas, and a dispersion system, as a field for performing manipulation to which the object component is to be subjected, the method further comprising, prior to the step (i), subjecting the manipulation vessel to the step of subjecting the sample to a predetermined manipulation and collecting the target substance.

26. The method according to claim 25, wherein the manipulation portion comprises a column for chromatography, and the manipulation medium comprises a filling material for chromatography and a developing solvent.

27. The method according to claim 25, wherein the manipulation vessel has a tubular shape, and the manipulation medium is a multi-layered object in which layers of an aqueous liquid and a gel are alternately stacked in a longitudinal direction.

28. The method according to claim 27, wherein the manipulation portion has an openably-closed sample supply portion for supplying a sample into the manipulation vessel, and after a step of supplying the sample, the accommodated substance is maintained in a completely hermetically-sealed state until the step (iv) is finished.

29. The method according to claim 25, wherein the manipulation medium comprises a droplet encapsulating medium and an encapsulated aqueous droplet.

* * * * *